United States Patent
Inokuchi et al.

(10) Patent No.: US 9,205,031 B2
(45) Date of Patent: Dec. 8, 2015

(54) COMPOSITE PARTICLES, METHOD FOR PREPARING THE SAME AND COSMETIC COMPOSITION

(75) Inventors: Yoshinori Inokuchi, Annaka (JP); Ryuichi Inaba, Tokyo (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 506 days.

(21) Appl. No.: 12/490,788

(22) Filed: Jun. 24, 2009

(65) Prior Publication Data

US 2010/0330132 A1 Dec. 30, 2010

(51) Int. Cl.

| | |
|---|---|
| *A61Q 5/12* | (2006.01) |
| *A61K 8/02* | (2006.01) |
| *A61K 8/19* | (2006.01) |
| *A61K 8/891* | (2006.01) |
| *A61K 8/892* | (2006.01) |
| *A61Q 1/00* | (2006.01) |
| *A61Q 1/06* | (2006.01) |
| *A61Q 1/10* | (2006.01) |
| *A61Q 1/12* | (2006.01) |
| *A61Q 5/00* | (2006.01) |
| *A61Q 15/00* | (2006.01) |
| *A61Q 17/04* | (2006.01) |
| *A61Q 19/00* | (2006.01) |

(52) U.S. Cl.
CPC ... *A61K 8/02* (2013.01); *A61K 8/19* (2013.01); *A61K 8/891* (2013.01); *A61K 8/892* (2013.01); *A61K 2800/413* (2013.01); *A61Q 1/00* (2013.01); *A61Q 1/06* (2013.01); *A61Q 1/10* (2013.01); *A61Q 1/12* (2013.01); *A61Q 5/00* (2013.01); *A61Q 5/12* (2013.01); *A61Q 15/00* (2013.01); *A61Q 17/04* (2013.01); *A61Q 19/00* (2013.01)

(58) Field of Classification Search
CPC ......... A61K 8/00; A61K 8/02; A61K 8/0241; A61K 8/0245; A61K 8/025; A61K 8/25; A61K 8/19
USPC ............ 424/464–480, 401, 501, 59, 65, 70.1, 424/70.12, 70.121
See application file for complete search history.

(56) References Cited

U.S. PATENT DOCUMENTS

| | | | |
|---|---|---|---|
| 3,159,601 A | 12/1964 | Ashby | |
| 3,159,662 A | 12/1964 | Ashby | |
| 3,220,972 A | 11/1965 | Lamoreaux | |
| 3,775,452 A | 11/1973 | Karstedt | |
| 5,028,653 A | 7/1991 | Desmonceau et al. | |
| 6,362,159 B1 * | 3/2002 | Aguadisch et al. | 512/4 |
| 6,825,259 B2 | 11/2004 | Miyazaki et al. | |
| 6,923,974 B2 | 8/2005 | Tanaka et al. | |
| 7,531,184 B2 | 5/2009 | Horino et al. | |
| 2003/0171475 A1 * | 9/2003 | Miyazaki et al. | 524/449 |
| 2005/0282002 A1 | 12/2005 | Husemann et al. | |
| 2008/0138621 A1 * | 6/2008 | Morita | 428/404 |
| 2009/0155586 A1 | 6/2009 | Maitra et al. | |

FOREIGN PATENT DOCUMENTS

| | | |
|---|---|---|
| EP | 0 958 805 A2 * | 5/1999 |
| EP | 0 958 805 A2 | 11/1999 |
| EP | 0 958 805 A2 * | 11/1999 |
| JP | 2-232263 A | 9/1990 |
| JP | 3-281536 A | 12/1991 |
| JP | 3-294357 A | 12/1991 |
| JP | 6-128122 A | 5/1994 |
| JP | 8-3451 A | 1/1996 |
| JP | 8-188723 A | 7/1996 |
| JP | 9-20609 A | 1/1997 |
| JP | 09-020631 A | 1/1997 |
| JP | 2000-319128 A | 11/2000 |
| JP | 2001-079980 A | 3/2001 |
| JP | 2002-047138 A | 2/2002 |
| JP | 2002-068937 A | 3/2002 |
| JP | 2002-69329 A | 3/2002 |
| JP | 2002-146238 A | 5/2002 |
| JP | 2002-154929 A | 5/2002 |
| JP | 2003-40737 A | 2/2003 |
| JP | 3702072 B2 | 10/2005 |
| JP | 2006-002151 A | 1/2006 |
| WO | WO 92/03119 A1 | 3/1992 |

OTHER PUBLICATIONS

Japanese Office Action dated Dec. 19, 2012 for Japanese Patent Application No. 2009-147553.
Extended European Search Report dated Jun. 4, 2014 for European Application No. 10251124.3.

* cited by examiner

*Primary Examiner* — Michael G Hartley
*Assistant Examiner* — Micah-Paul Young
(74) *Attorney, Agent, or Firm* — Birch, Stewart, Kolasch & Birch, LLP

(57) ABSTRACT

Composite particles formed of core particles and a silicone elastomer adhered to surfaces of the core particles.

16 Claims, 1 Drawing Sheet

COMPOSITE PARTICLES, METHOD FOR PREPARING THE SAME AND COSMETIC COMPOSITION

BACKGROUND ART

This invention relates to composite particles comprising core particles and a silicone elastomer adhered to the surfaces of the core particles, a method for preparing the same, and a cosmetic composition containing the composite particles.

A makeup cosmetic composition such as a foundation is to conceal skin configuration troubles such as wrinkles, pores and texture roughness and skin tone troubles such as blemishes and freckles, and gives a smooth and beautiful look to skin. In recent years, a non-artificial natural finish feel (bare skin feel) is considered to be important. A cosmetic composition is assessed to provide a natural finish feel, when the cosmetic composition is free of unnatural gloss (shine), is excellent in the uniformity of the adhesion of a cosmetic film, and has high transparency. Numerous new materials and new technologies have conventionally been proposed to provide a natural finish feel while retaining the above-described effects of makeup cosmetics. Especially for concealing configuration troubles, cosmetics having various diffuse reflectance powders blended therein are known. Proposed in JP-A 6-128122 (Patent Document 1) is a wrinkle-concealing, multilayer cosmetic making in which a makeup foundation containing a tacky substance for a first layer, and a makeup finish containing a powder that diffuses and reflects light for a second layer are used in combination. In this wrinkle-concealing, multilayer cosmetic, composite powder of the light diffuse reflectance type obtained by coating talc particles with an acrylic polymer is used, for example.

This cosmetic composition is, however, accompanied by a drawback that, when a cosmetic film is held for a long time on the skin, the powder and the tacky substance fall outside an appropriate mixing range due to mixing of sebum to the tacky substance, leading to reductions in its effects. The pamphlet of PCT Patent Publication No. WO 92/03119 (Patent Document 2) discloses a flaky fine powder composed of a flaky substance such as natural mica and spherical, fine particulate silica coated on the surfaces of the flaky substance. Because this flaky fine powder uses the spherical fine particles having high surface diffuse reflectance effects for light, the use of this flaky fine powder as a cosmetic additive is described to bring about technical effects that "the gloss of mica as a base at corners thereof can be reduced, a soft focus effect such as making fine wrinkles less noticeable can be exhibited, and further, cosmetics far improved in slipperiness and touch feel in use can be obtained."

For the extremely good slipperiness of the flaky fine powder, however, a cosmetic composition having the flaky fine powder blended therein involves a drawback that it tends to form creases upon application, can be hardly applied evenly, and cannot obtain a natural finish. In addition, the fine particulate silica employed as a coating material decreases the area of contact between the composite powder and the skin. The cosmetic composition is, therefore, accompanied by another drawback that the fine particulate silica reduces the adhesion to the skin, renders the composite powder susceptible to falling off from the skin by physical impacts such as rubbing by clothing, and lowers the retention of the effects of the cosmetic. Further, any attempt to lower the proportion of the fine particulate silica in the flaky fine powder with a view to improving the adhesion of the composite powder to the skin results in a drawback that the effects for configuration troubles cannot be obtained sufficiently.

Other technologies which are similar to the foregoing technologies and are intended to avoid configuration troubles or to bring about a natural finish feel include a cosmetic composition that contains a pigment of the core-shell structure obtained by coating a flaky extender pigment as cores with a colored-pigment-containing titanium dioxide and further coating the coated cores with a light-diffusing powder (JP-A 8-188723; Patent Document 3), a technology that mixes in a cosmetic composition composite powder obtained by coating surfaces of a clay mineral with an inorganic metal hydroxide such as aluminum hydroxide (JP-A 9-20609, Patent Document 4; JP-A 2002-146238, Patent Document 5), a cosmetic composition that contains powder having layers of a high-refractive-index metal oxide coated on surfaces of powder having a refractive index of from 1.6 to 1.7 such as barium sulfate and layers of one or more materials, which are selected from yellow iron oxide, black iron oxide and red iron oxide, coated on the first-mentioned layers (JP-A 2003-40737, Patent Document 6), a cosmetic composition obtained by mixing in the cosmetic composition a silica-zinc oxide composite material obtained by combining silica sol and zinc oxide (Japanese Patent No. 3702072, Patent Document 7).

These composite powders each exhibit a certain degree of soft focus effect owing to their light diffusing effect. When attention is paid to a feel upon use of each cosmetic composition, however, the cosmetic composition is not fully satisfactory in softness, moistness, and smoothness for the hardness of the composite powder itself because the composite powder is composed of the inorganic metal oxide or inorganic metal hydroxide. For the purpose of improving the feel on use of such a cosmetic powder, specifically, imparting a feel on use such as a freely flowing feel and smoothness, spreadability, adhesiveness and the like, on the other hand, JP-A 2002-69329 (Patent Document 8) proposes particles obtained by coating surfaces of scaly inorganic particles with a polyurethane, styrene-butadiene copolymer, silicone-based elastomer or polyolefin-based elastomer, and describes that a soft and moist feel can be obtained.

However, no specific exemplification is made as to the particles coated with such a silicone-based elastomer. In yet further documents, particles with silicone elastomers coated on surfaces of particles and their making methods are proposed. Proposed in JP-A 8-3451 (Patent Document 9) is a method that mixes a silicone elastomer having reactive functional groups and silica to crush them. This method is, however, accompanied by a drawback that, because the silica particles as core particles are crushed, particles cannot be obtained with the initial shape and particle size. In other words, particles in the form of a specific shape such as sphere, plate or rod cannot be obtained, and the particle size can be hardly controlled. JP-A 3-294357 (Patent Document 10) proposes a method that mixes core particles with a curable silicone composition which would cure into a silicone elastomer, and then cures the silicone composition. The resulting particles, however, contain plural core particles therein. JP-A 2-232263 (Patent Document 11) proposes a method that emulsifies and disperses in water a mixture of silica particles as core particles and a curable silicone composition which would cure into a silicone elastomer and then cures the silicone composition, and JP-A 3-281536 (Patent Document 12) proposes a method that emulsifies and disperses in water a mixture of an aqueous dispersion of silica particles and a curable silicone composition which would cure into a silicone elastomer and then cures the silicone composition. These methods, however, form particles containing plural core particles therein or particles containing no core particles therein.

DISCLOSURE OF THE INVENTION

As mentioned above, the technologies proposed to date were difficult to obtain a powder which can impart natural finish feel and pleasant feel upon use to a cosmetic composition at the same time. Therefore, an object of the present invention is to provide composite particles, which are good in spreadability, softness, adhesion and mixing conditions and are excellent in skin-configuration correcting effects, and also provide a method for preparing such composite particles and a cosmetic composition containing the composite particles.

The present inventors have earnestly studied to achieve the above-described object. As a result, it has been found that by causing a silicone elastomer having light diffusing effect to adhere to the surfaces of core particles, there is obtained composite particles which can visually improve the effect of decreasing skin configuration trouble, give freely flowing effect and moist feel inherent to the silicone elastomer upon use, assure good spreadability, softness, adhesion and mixing state, and impart skin-configuration correcting effect. Cosmetic compositions having such composite particles blended therein also have the same effect. The present invention is based on the above finding. In this case, by using a silicone resin as a binder when the silicone elastomer is subjected to adhering to the core particles, the above effects are more exerted.

Therefore, the present invention provides the following composite particles and method for preparing such composite particles, and cosmetic composition containing the composite particles:

[1] Composite particles comprising core particles and a silicone elastomer adhered to the surfaces of the core particles.
[2] The composite particles as described above in [1], wherein the core particles are inorganic particles, organic particles or composite inorganic-organic particles.
[3] The composite particles as described above in [1], wherein the silicone elastomer is adhered to the surfaces of the core particles by a silicone resin binder.
[4] The composite particles as described above in [3], which is obtained by adding an acidic substance or alkaline substance and a compound selected from alkoxysilanes and silanol-containing silanes and partial condensation products thereof to a mixed aqueous dispersion having the core particles and a silicone elastomer dispersed therein and subjecting the compound to a hydrolytic condensation reaction, thereby causing the silicone elastomer to adhere to the surfaces of the core particles.
[5] The composite particles as described above in [4], wherein the mixed aqueous dispersion further comprises a surfactant.
[6] A method for preparing composite particles comprising core particles and a silicone elastomer adhered to the surfaces of the core particles, the method comprising the steps of: adding an acidic substance or alkaline substance and a compound selected from alkoxysilanes and silanol-containing silanes and partial condensation products thereof to a mixed aqueous dispersion having the core particles and silicone elastomer dispersed therein; and subjecting the compound to a hydrolytic condensation reaction.
[7] The method as described above in [6], wherein the mixed aqueous dispersion further comprises a surfactant.
[8] A cosmetic composition comprising the composite particles as described above in any one of [1] to [5].

According to the present invention, it is possible to provide composite particles which are good in spreadability, softness, adhesion and mixing state and are excellent in skin-configuration correcting effects, and a method for preparing such composite particles and a cosmetic composition containing the composite particles.

BEST MODE FOR CARRYING OUT THE INVENTION

Figure 1:
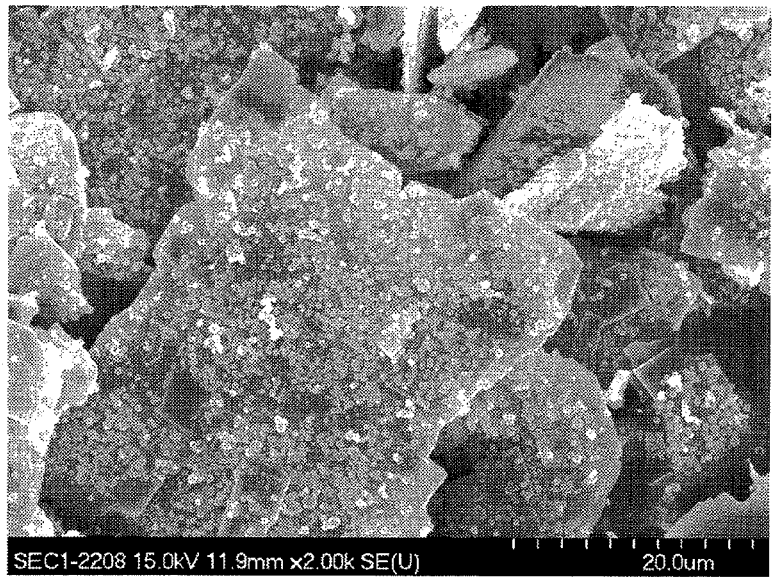
FIG. 1 is an electron micrograph of composite particles obtained in Example 1.
Figure 2:
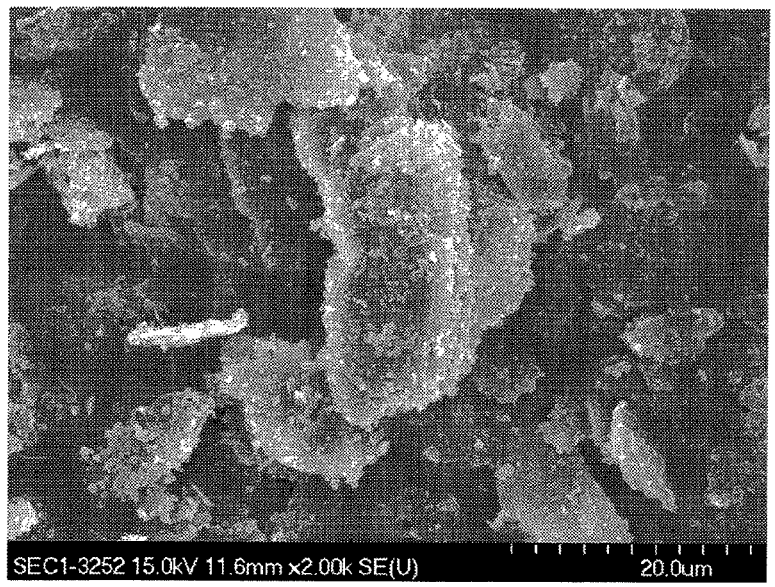
FIG. 2 is an electron micrograph of composite particles obtained in Example 2.

The following is the detailed description of the invention in the order of I. Composite particles,
II. Preparing method of the composite particles, and
III. Cosmetic compositions containing the composite particles.
I. Composite Particles Composite particles according to the present invention comprises core particles and a silicone elastomer adhered to the surfaces of the core particles, and preferably, are particles having the silicone elastomer adhered to the core particles by a silicone resin binder.

[Core Particles]

The core particles include inorganic particles, organic particles, or composite organic-inorganic particles. These inorganic particles, organic particles, and composite organic-inorganic particles can be used either singly or in combination as desired. Any core particles having any particle size practically usable in cosmetics are applicable. Further, the core particles can have any geometrical form insofar as the core particles are generally usable in cosmetics, and can be of any shape such as spheres, polygons, spindles, needles or plates. In addition, the core particles can be either nonporous or porous.

The average particle size may preferably be in a range of from 0.5 to 50 μm, more preferably from 1 to 30 μm. A particle size smaller than 0.5 μm may lead to reductions in feel upon use, such as freely flowing property and smoothness, and spreadability-imparting effect, while a particle size greater than 50 μm may result in a coarse feel. It is to be noted that each average particle size is measured by suitably choosing the microscope method, the light scattering method, the laser diffraction method, the liquid-phase precipitation method, or the electrical resistance method in accordance with the corresponding shape.

The inorganic particles include particles of titanium oxide, mica titanium, zirconium oxide, zinc oxide, cerium oxide, magnesium oxide, barium sulfate, calcium sulfate, magnesium sulfate, calcium carbonate, magnesium carbonate, talc, cleaved talc, mica, kaolin, sericite, muscovite, synthetic mica, phlogopite, lepidolite, biotite, lithia mica, silicic acid, silicon dioxide, hydrated silicon dioxide, aluminum silicate, magnesium silicate, aluminum magnesium silicate, calcium silicate, barium silicate, strontium silicate, a metal tungstate, hydroxyapatite, vermiculite, "HIGILITE," bentonite, montmorillonite, hectorite, zeolite, ceramics, calcium secondary phosphate, alumina, aluminum hydroxide, boron nitride, boron nitride, glass or the like.

An inorganic pigment can also be used as the inorganic particles. Specific examples include inorganic red pigments such as iron oxide, iron hydroxide and iron titanate; inorganic brown pigments such as γ-iron oxide; inorganic yellow pigments such as yellow iron oxide and ocher; inorganic black pigments such as black iron oxide and carbon black; inorganic violet pigments such as manganese violet and cobalt violet; inorganic green pigments such as chromium hydroxide, chromium oxide, cobalt oxide and cobalt titanate; inorganic blue pigments such as prussian blue and ultramarine; colored pigments such as laked tar-based colorants and laked natural colorants; pearlescent pigments such as mica coated with titanium oxide, mica coated with titanium oxide, bismuth oxychloride, bismuth oxychloride coated with titanium oxide, talc coated with titanium oxide, argentine, and color mica coated with titanium oxide; and metal powder pigments such as aluminum powder, copper powder, and stainless steel powder.

The organic particles include particles of a polyamide, polyacrylic acid-acrylic acid ester, polyester, polyethylene, polypropylene, polystyrene, styrene-acrylic acid copolymer, divinylbenzene-styrene copolymer, polyurethane, vinyl resin, urea resin, melamine resin, benzoguanamine, polymethylbenzoguanamine, tetrafluoroethylene, polymethyl methacrylate such as polymethyl methacrylate, cellulose, silk, nylon, phenol resin, epoxy resin, polycarbonate, or the like.

Particles of a surfactant metal salt (metallic soap) can also be used. Specific examples include zinc stearate, aluminum stearate, calcium stearate, magnesium stearate, zinc myristate, magnesium myristate, zinc cetyl phosphate, calcium cetyl phosphate, and zinc sodium cetyl phosphate.

An organic pigment can also be used. Specific examples include tar colorants such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and natural colorants such as carminic acid, laccaic acid, carthamin, brazilin, and crocin.

The composite inorganic-organic particles can be composite particles obtained by coating the surfaces of inorganic particles, which are commonly usable in cosmetics, with organic particles by a conventional method.

The core particles may be surface treated with a metallic soap, silane, silicone, silicone resin, fluorine-containing compound, amino acid, iron oxide, titanium oxide, iron oxide and titanium oxide, or aluminum hydroxide. Especially when particles capable of exhibiting relatively high light diffusing effect compared with other particles for cosmetics are adopted, it is possible, in combination with the light diffusing effect of the silicone elastomer, to further improve the concealing effect for configuration troubles such as wrinkles by diffusing light on the surfaces of the composite particles or inside the composite particles and decreasing a difference in brightness between dermal ridges and dermal furrows. Examples of the particles include barium sulfate, aluminum oxide, barium sulfate treated with iron oxide, barium sulfate treated with titanium oxide, barium sulfate treated with iron oxide and titanium oxide, mica treated with aluminum hydroxide, titanium oxide, iron oxide, and the like. From the standpoint of thin, uniform, soft and smooth spreadability, mica, sericite, talc, cleaved talc, mica titanium, mica titanium treated with iron oxide, and the like are also preferred.

[Silicone Elastomer]

In the present invention, the silicone elastomer may be adhered to the surfaces of the core particles in any form. Further, no particular limitation is imposed on the consistency at which the silicone elastomer is adhered to the surfaces of the particles, insofar as the advantageous effects to be achieved by the present invention are exhibited. For example, a silicone elastomer in the form of particles may adhere sparsely to the particle surfaces, a silicone elastomer in the form of particles may cover and adhere to the particle surfaces with no space, a silicone elastomer having no particulate shape may adhere in the form of networks to the particle surfaces, or a silicone elastomer may cover and adhere in the form of films to the particle surfaces; or a silicone elastomer may adhere to the particle surfaces in a combination of such forms.

The silicone elastomer in the present invention can be produced, for example, by a method wherein a curable liquid silicone composition is emulsified as described later. Accordingly, its shape is spherical in many instances. Depending on the reaction conditions, the effects will not significantly impaired no matter whether the silicone elastomer is substantially spherical or is in the form of partially aggregated particles. From the standpoint of having the feel on use of the elastomer exhibited effectively, the elastomer may preferably be smaller than core particles to which the elastomer is caused to adhere. If the elastomer is greater than the core particles, the characteristic properties of the particles including the feel like freely flowing property and smoothness upon use, spreadability and adhesiveness may not be exhibited. No particular limitation is imposed on the lower limit of the particle size. The lower limit may be the minimum particle size obtained by the method wherein a liquid silicone composition is emulsified.

The silicone elastomer is a rubber elastomer having linear organosiloxane blocks represented by the following formula (1):

$$-(R^1{}_2SiO_{2/2})_n- \tag{1}$$

wherein $R^1$ is a substituted or unsubstituted monovalent hydrocarbon group having from 1 to 30 carbon atoms, and n is a positive number of from 5 to 5,000. Examples of $R^1$ in the formula include alkyl groups such as methyl, ethyl, propyl, butyl, pentyl, hexyl, heptyl, octyl, nonyl, decyl, undecyl, dodecyl, tetradecyl, pentadecyl, hexadecyl, heptadecyl, octadecyl, nonadecyl, eicosyl, henicosyl, docosyl, tricosyl, tetracyl, and triacotyl; cycloalkyl groups such as cyclobutyl, cyclopentyl, cyclohexyl, and cycloheptyl; aryl groups such as phenyl, tolyl and naphthyl; aralkyl groups such as benzyl, phenethyl and β-phenylpropyl; alkenyl groups such as vinyl and allyl; and hydrocarbon groups formed by substituting some or all of the hydrogen atoms bonded to the carbon atoms of these groups with atoms such as halogen atoms (fluorine atoms, chlorine atoms, bromine atoms, iodine atoms) and/or substituent groups such as acryloyloxy, methacryloyloxy, epoxy, glycidoxy, amino, mercapto and carboxyl.

As the rubber hardness of the silicone elastomer, a lower hardness may preferably be 10 or higher as measured by a type E durometer as specified in JIS K 6253, and a higher hardness may preferably be 90 or lower as measured by a type A durometer. More preferably, the rubber hardness may be in a range of 20 or higher by the type E durometer but 80 or lower by the type A durometer. A rubber hardness of lower than 10 by the type E durometer may result in higher cohesive property and may lead to reductions in the feel such freely flowing property and smoothness upon use, and spreadability. On the other hand, a rubber hardness of higher than 90 by the type A durometer may lead to a reduction in a soft touch feel. The silicone elastomer can be one having tackiness unless it substantially reduces the feel such as freely flowing property and smoothness upon use, and spreadability. The silicone elastomer may contain in its particles ingredients approved for cosmetics, such as silicone oils, organosilanes, silicone resins, inorganic particles, organic particles, and liquid oils like hydrocarbon-based oils.

A silicone elastomer is obtained from a curable liquid silicone composition. The composition may be cured, for example, through a condensation reaction between methoxysilyl groups ($\equiv$SiOCH$_3$) and hydroxysilyl groups ($\equiv$SiOH) or between hydrosilyl groups ($\equiv$SiH) and hydroxysilyl groups ($\equiv$SiOH), a radical reaction between mercaptopropylsilyl groups ($\equiv$Si—C$_3$H$_6$SH) and vinylsilyl groups ($\equiv$SiCH=CH$_2$), an addition reaction between vinylsilyl groups ($\equiv$SiCH=CH$_2$) and hydrosilyl groups ($\equiv$SiH), or the like. From the standpoint of reactivity, it is preferred to rely upon the condensation reaction or the addition reaction.

When forming a silicone elastomer by curing through an addition reaction, for example, a curable liquid silicone composition—in which an organopolysiloxane represented by the following average compositional formula (2):

and having at least two monovalent olefinic unsaturated groups per molecule, and an organohydrogenpolysiloxane represented by the following average compositional formula (3):

and having at least three hydrogen atoms bonded to a silicon atom per molecule, are mixed at a ratio such that from 0.5 to 2 hydrosilyl groups are contained per the monovalent olefinic unsaturated group—may be subjected to addition polymerization in the presence of a platinum-based catalyst.

In the formula, $R^2$ is a substituted or unsubstituted monovalent hydrocarbon group having from 1 to 30 carbon atoms other than an aliphatic unsaturated group, $R^3$ is a monovalent olefinic unsaturated group having from 2 to 6 carbon atoms, and a and b are positive numbers defined by $0<a<3$, $0<b\leq3$, and $0.1\leq a+b\leq3$, preferably by $0<a\leq2.295$, $0.005\leq b\leq2.3$, and $0.5\leq a+b\leq2.3$.

In the formula, $R^4$ is a substituted or unsubstituted, monovalent hydrocarbon group having from 1 to 30 carbon atoms other than an aliphatic unsaturated group, and c and d are positive numbers defined by $0<c<3$, $0<d\leq3$, and $0.1\leq c+d\leq3$, preferably by $0<c\leq2.295$, $0.005\leq d\ 2.3$, and $0.5\leq c+d\leq2.3$.

Examples of $R^2$ include alkyl groups such as methyl, ethyl, propyl, butyl, pentyl, hexyl, heptyl, octyl, nonyl, decyl, undecyl, dodecyl, tetradecyl, pentadecyl, hexadecyl, heptadecyl, octadecyl, nonadecyl, eicosyl, henicosyl, docosyl, tricosyl, tetracyl, and triacotyl; cycloalkyl groups such as cyclobutyl, cyclopentyl, cyclohexyl, and cycloheptyl; aryl groups such as phenyl, tolyl and naphthyl; aralkyl groups such as benzyl, phenethyl and β-phenylpropyl; and hydrocarbon groups formed by substituting some or all of the hydrogen atoms bonded to the carbon atoms of these groups with atoms such as halogen atoms (fluorine atoms, chlorine atoms, bromine atoms, iodine atoms) and/or substituent groups such as acryloyloxy, methacryloyloxy, epoxy, glycidoxy, and carboxyl. In $R^2$s, non-reactive groups such as alkyl, aryl, aralkyl and cycloalkyl may desirably account for 80 mole % or more, preferably 90 mole % or more.

Examples of $R^3$ include a vinyl, allyl, butenyl, pentenyl, hexenyl or like group, although a vinyl group is preferred industrially. As $R^4$, those similar to the examples of $R^2$ can be exemplified.

The viscosities at 25° C. of the organopolysiloxane having the olefinic unsaturated groups, and the organohydrogenpolysiloxane, respectively, may be preferably 1,000,000 mm$^2$/s or lower, more preferably 500,000 mm$^2$/s or lower, because viscosities higher than 1,000,000 mm$^2$/s make it unable to obtain particles of small particle size in the production described later. The structures of the organopolysiloxane having the olefinic unsaturated groups, and organohydrogenpolysiloxane, respectively, may be linear, cyclic or branched. The viscosities are measurement values by a capillary viscometer.

Examples of the platinum-based catalyst include platinum group metal elements such as platinum (including platinum black), rhodium and palladium; platinum chloride, chloroplatinic acid and chloroplatinate salts such as H$_2$PtCl$_4$.kH$_2$O, H$_2$PtCl$_6$.kH$_2$O, NaHPtCl$_6$.kH$_2$O, KHPtCl$_6$.kH$_2$O, Na$_2$PtCl$_6$.kH$_2$O, K$_2$PtCl$_4$.kH$_2$O, PtCl$_4$.kH$_2$, PtCl$_2$ and Na$_2$HPtCl$_4$.kH$_2$O (in which k is an integer of from 0 to 6, preferably 0 or 6); alcohol-modified chloroplatinic acids (see U.S. Pat. No. 3,220,972); complexes between chloroplatinic acid and olefins (see U.S. Pat. Nos. 3,159,601, 3,159,662 and 3,775,452); platinum group metals, such as platinum black and palladium, supported on carriers such as alumina, silica and carbon; rhodium-olefin complexes; chlorotris(triphenylphosphine)-rhodium (Wilkinson's catalyst); complexes between platinum chloride, chloroplatinic acid or chloroplatinate salts and vinyl-containing siloxanes, especially vinyl-containing siloxanes; and the like.

When forming a silicone elastomer by curing through a condensation reaction, for example, a liquid silicone composition comprising an organopolysiloxane having at least two hydroxyl groups bonded to a silicon atom per molecule, and an organohydrogenpolysiloxane having at least three hydrogen atoms bonded to a silicon atom per molecule, may be subjected to condensation polymerization in the presence of a condensation catalyst.

No particular limitation is imposed on the amount of the silicone elastomer insofar as the advantageous effects to be achieved by the present invention are exhibited. When a more pronounced soft focus effect and a good feel such as freely flowing property and smoothness upon use, spreadability, moist feel and softness is desired, the amount of the silicone elastomer may be preferably 0.5 parts by weight or more, more preferably 1 parts by weight or more, still more preferably 2 parts by weight or more per 100 parts by weight of the core particles. However, a large amount of the silicone elastomer may result in higher cohesive property and may hence lead to reductions in a feel such as freely flowing property and smoothness upon use, and spreadability. Therefore, the amount of the silicone elastomer may be preferably 100 parts by weight or smaller, more preferably 70 parts by weight or smaller, still more preferably 50 parts by weight or smaller per 100 parts by weight of the core particles.

[Silicone Resin]

In the present invention, it is preferred to use a silicone resin as a binder for adhesion between the core particles and the silicone elastomer. When the composite particles are formed by causing the silicone elastomer to adhere to the surfaces of the core particles by using the silicone resin as a binder, the silicone elastomer can be fixedly secured on the surfaces of the core particles to make the silicone elastomer resistant to fall-off from the surfaces of the core particles, the adhesion of the silicone elastomer can be provided with higher evenness, and a still better feel on use can be given. The silicone resin may adhere locally or entirely to the surfaces of the core particles and/or the surfaces of the silicone elastomers.

The silicone resin in the present invention is a polymer formed of one or more of structural units selected from $[R^5SiO_{3/2}]$, $[R^5_2SiO_{2/2}]$, $[R^5_3SiO_{1/2}]$ and $[SiO_{4/2}]$ and including at least [R⁵SiO₃/₂] or [SiO₄/₂]. In these formulas, R⁵ is independently a monovalent organic group having from 1 to 20 carbon atoms. In a manner to be described later, the silicone resin is produced by a hydrolytic condensation reaction of at least one compound selected from alkoxysilanes and silanol-containing silanes and their partial condensation products. However, a portion of the compound does not undergo the condensation reaction, and silanol groups remain unreacted. More specifically, the silicone resin is a copolymer also including structural units selected from the following silanol-containing structural units.

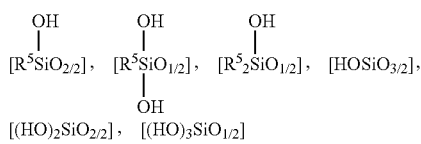

Unless the silicone resin is a structural member including [R⁵SiO₃/₂] or [SiO₄/₂], it cannot become a resinous solid matter. No particular limitation is imposed on the proportions of the structural units, the polymerization degree and the hardness, provided that the silicone resin is a resinous solid matter at room temperature and is insoluble in cosmetic oils useful in such cosmetics as will be described later. If the melting point is low, however, the composite particles themselves may fuse together during storage in an atmosphere of high temperature or in a drying step. Therefore, the melting point may be preferably 50° C. or higher, more preferably 80° C. or higher. As a large proportion of [SiO₄/₂] units results in reduced slipperiness, a polymer formed of one or more structural units selected from [R⁵SiO₃/₂], [R⁵₂SiO₂/₂] and [R⁵₃SiO₁/₂] and always including [R⁵SiO₃/₂] is preferred. More preferred is a structure in which [R⁵SiO₃/₂] units account for 50 mole % or more, with 70 mole % or more being still more preferred.

Examples of R⁵ in the above-described formulas include alkyl groups such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl; cycloalkyl groups such as cyclobutyl, cyclopentyl, cyclohexyl, and cycloheptyl; aryl groups such as phenyl, tolyl and naphthyl; aralkyl groups such as benzyl, phenethyl and β-phenylpropyl; alkenyl groups such as vinyl and allyl; and hydrocarbon groups formed by substituting some or all of the hydrogen atoms bonded to the carbon atoms of these groups with atoms such as halogen atoms (fluorine atoms, chlorine atoms, bromine atoms, iodine atoms) and/or substituent groups such as acryloyloxy, methacryloyloxy, epoxy, glycidoxy, amino, mercapto and/or carboxyl groups. In the manner to be described later, the resinous silicone is produced by the hydrolytic condensation reaction of the one or more compounds selected from the alkoxysilanes and silanol-containing silanes and their partial condensation products. In view of the condensation reactivity of the one or more compounds, methyl groups may amount preferably at least 50 mole %, more preferably at least 70 mole % of R⁵s.

When a silicone resin is used as a binder, no particular limitation is imposed on its amount. From the standpoint of further increasing the evenness of adhesion of the silicone elastomer, the amount of the silicone resin may be preferably 10 parts by weight or more, more preferably 20 parts by weight or more, still more preferably 30 parts by weight or more per 100 parts by weight of the silicone elastomer. When the amount of the silicone resin becomes greater, the soft feel of the silicone elastomer may not be exhibited. The amount of the silicone resin may be preferably 500 parts by weight or smaller, more preferably 300 parts by weight or smaller, still more preferably 200 parts by weight or smaller per 100 parts by weight of the silicone elastomer.

The composite particles according to the present invention are particles formed of core particles and a silicone elastomer adhered on surfaces of the core particles, preferably, by using a silicone resin binder. There is no problem even when the particles are surface treated with a silylating agent, silicone oil, wax, paraffin, organic fluorine-containing compound, surfactant or the like to impart or improve water repellency or to improve the dispersibility in a cosmetic oil.

The state of the silicone elastomer adhered on the surfaces of the core particles can be observed under an electron microscope. The particle size of the adhered silicone elastomer may be preferably from 50 nm to 1 μm, more preferably from 100 to 800 nm. It is to be noted that this particle size can be determined by an electron microscope.

II. Preparing Method of the Composite Particles

Composite particles composed of core particles and a silicone elastomer adhered to surfaces of the core particles by a silicone resin binder can be obtained, for example, by adding an acidic substance or alkaline substance and at least one compound selected from alkoxy silanes and silanol-containing silanes and partial condensation products thereof to a mixed aqueous dispersion in which core particles and a silicone elastomer have been dispersed, and subjecting the compound to a hydrolytic condensation reaction.

The amount of the core particles may be preferably from 3 to 150 parts by weight, more preferably from 5 to 50 parts by weight per 100 parts by weight of water to be used. An amount smaller than 3 parts by weight may lead to a deterioration in efficiency, while an amount greater than 150 parts by weight results in the mixed aqueous dispersion having a higher viscosity, thereby possibly making it difficult to cause the silicone elastomer to adhere to the core particles. The core particles may be used in the form of an aqueous dispersion prepared beforehand.

No particular limitation is imposed on preparing the silicone elastomer, and a method conventionally known for the preparation of a dispersion of a silicone elastomer can be used. The silicone elastomer can be produced, for example, by emulsifying a curable liquid silicone composition in water while using a surfactant and then subjecting the curable liquid silicone composition to a curing reaction. To form a silicone elastomer by achieving curing through an addition reaction, for example, there is a method wherein a surfactant and water are added to a curable liquid silicone composition comprising the above-described organopolysiloxane containing the olefinic unsaturated groups and organohydrogenpolysiloxane to form an emulsion, and then adding a platinum-based catalyst to conduct addition polymerization.

Alternatively, there is a method using a curable liquid silicone composition produced by emulsion polymerization. To form a silicone elastomer by achieving curing through a condensation reaction, for example, there is a method to be described hereinafter. A surfactant and water are added to a cyclopolysiloxane, which is represented by the formula [R⁶₂SiO]ₘ in which R⁶ is a substituted or unsubstituted, monovalent hydrocarbon group having from 1 to 30 carbon atoms and m is a number of from 3 to 7, to conduct emulsification. After an acid is added to conduct a polymerization reaction, an alkali is added to effect neutralization to prepare an emulsion of an organopolysiloxane having hydroxyl groups bonded to silicon atoms at opposite ends of a linear molecule respectively. An organotrialkoxysilane and a condensation catalyst are added to the emulsion to conduct condensation polymerization.

No particular limitation is imposed on the surfactant to be used for the emulsification of the curable liquid silicone composition. Examples include nonionic surfactants such as polyoxyethylene alkyl ethers, polyoxyethylene polyoxypropylene alkyl ethers, polyoxyethylene alkylphenyl ethers, polyethylene glycol fatty acid esters, sorbitan fatty acid esters, polyoxyethylene sorbitan fatty acid esters, polyoxyethylene sorbit fatty acid esters, glycerin fatty acid esters, polyoxyethylene glycerin fatty acid esters, polyglycerin fatty acid esters, propylene glycol fatty acid esters, polyoxyethylene propylene glycol fatty acid esters, polyoxyethylene caster oil, polyoxyethylene hydrogenated castor oil, polyoxyethylene hydrogenated castor oil fatty acid esters, polyoxyethylene phytostanol ether, polyoxyethylene phytosterol ether, polyoxyethylene cholestanol ether, polyoxyethylene cholesteryl ether, polyoxyethylene alkylamines, alkyl alkanol amides, sucrose fatty acid esters, methyl glucoside fatty acid esters, alkyl polyglycosides, linear or branched polyoxyethylene-modified organopolysiloxanes, linear or branched polyoxyethylene/polyoxypropylene-modified organopolysiloxanes, polyoxyethylene-alkyl co-modified organopolysiloxanes, linear or branched polyoxyethylene/polyoxypropylene-alkyl co-modified organopolysiloxanes, linear or branched polyglycerin-modified organopolysiloxanes, linear or branched polyglycerin-alkyl co-modified organopolysiloxanes, polyvinyl alcohol, polyvinylpyrrolidone, methylcellulose, and hydroxypropyl methyl cellulose; anionic surfactants such as alkyl sulfate ester salts, polyoxyethylene alkyl ether sulfate ester salts, polyoxyethylene alkylphenyl ether sulfate ester salts, sulfate ester salts of fatty acid alkylolamides, alkyl benzene sulfonates, polyoxyethylene alkyl phenyl ether sulfonates, α-olefin sulfonate salts, α-sulfo-fatty acid ester salts, alkylnaphthalenesulfonic acids, alkyl diphenyl ether disulfonate salts, alkanesulfonate salts, N-acyl taurate salts, dialkylsulfosuccinate salts, monoalkylsulfosuccinate salts, polyoxyethylene alkyl ether sulfosuccinate salts, fatty acid salts, polyoxyethylene alkyl ether carboxylate salts, N-acylamino acid salts, monoalkyl phosphate ester salts, dialkyl phosphate ester salts, polyoxyethylene alkyl ether phosphate ester salts, carboxymethylcellulose, polyacrylate salts, polystyrenesulfonate salts, naphthalene sulfonate salt-formalin condensation products, aromatic sulfonate salt-formalin condensation products, carboxyvinyl polymer, and styrene-oxyalkylenic anhydride copolymers; cationic surfactants such as alkyltrimethylammonium salts, dialkyldimethylammonium salts, polyoxyethylene alkyldimethylammonium salts, dipolyoxyethylene alkylmethylammonium salts, tripolyoxyethylene alkyl ammonium salts, alkylbenzyldimethylammonium salts, alkylpyridium salts, monoalkylamine salts, dialkylamine salts, trialkylamine salts, monoalkylamidoamine salts, and cationized cellulose; and amphoteric surfactants such as alkyldimethylamine oxides, alkyldimethylcarboxybetaines, alkylamidopropyl dimethylcarboxybetaines, alkylhydroxysulfobetaines, and alkylcarboxymethylhydroxyethylimidazoliniuim betaines. These surfactants can be used either singly or in combination as desired. The amount of the surfactant to be used may preferably be in a range of from 0.1 to 50 parts by weight per 100 parts by weight of the curable liquid silicone composition.

Upon conducting emulsification, a general emulsifier/disperser may be used. Its examples include high-speed centrifugal radial mixers such as a homodisper, high-speed shear mixers such as a homomixer, high-pressure jetting emulsifiers/dispersers such as a homogenizer, colloid mills, ultrasonic emulsifiers, and the like.

The resulting aqueous dispersion of the silicone elastomer may preferably be used as it is without being subjected to solid-liquid separation. The mixed aqueous dispersion in which the core particles and the silicone elastomer are dispersed can be obtained, for example, by mixing the core particles, the dispersion of the silicone elastomer, and, optionally, water. It is preferred to contain a surfactant in the mixed aqueous dispersion in which the core particles and the silicone elastomer are dispersed. When a silicone elastomer has been produced using a surfactant as described above, the surfactant is already contained in the aqueous dispersion of the silicone elastomer. Depending on circumstances, a surfactant may be further added to improve the dispersibility of the core particles and also to improve the evenness of the silicone elastomer to be coated on the surfaces of the core particles. No particular limitation is imposed on the surfactant to be added further, and the above-described surfactants for use in the emulsification of the curable liquid silicone can also be exemplified. It can be the same surfactant as that mixed in the aqueous dispersion of the silicone elastomer. Two or more surfactants may be added further. The amount of the surfactant(s) contained in the mixed aqueous dispersion of the core particles and silicone elastomer may preferably be from 0.01 to 3 parts by weight per 100 parts by weight of water.

The acidic substance or alkaline substance is a catalyst for the hydrolytic condensation reaction of the alkoxysilanes and silanol-containing silanes and their partial condensation products. The acidic substance or alkaline substance is added to the mixed aqueous dispersion in which at least the core particles and the silicone elastomer are dispersed. No particular limitation is imposed on the order of addition. After charging the acidic substance or alkaline substance beforehand, other ingredients may be added. Alternatively, after charging some of the other ingredients, the acidic substance or alkaline substance may be added, followed by addition of the remaining ingredients one after another.

The amount of the acidic substance to be added is such an amount that the pH of the mixed aqueous dispersion containing at least the acidic substance, the core particles and the silicone elastomer falls within a range of preferably from 1.0 to 4.0, more preferably from 1.5 to 3.5. When the acidic substance is added in an amount sufficient to control the pH to from 1.0 to 4.0, the hydrolytic condensation reaction of the compound selected from the alkoxysilanes and silanol-containing silanes and their partial condensation products is allowed to proceed sufficiently.

The amount of the alkaline substance to be added is such an amount that the pH of a mixed aqueous dispersion containing at least the alkaline substance, the core particles and the silicone elastomer falls within a range of preferably from 10.0 to 13.0, more preferably from 10.5 to 12.5. When the alkaline substance is added in an amount sufficient to control the pH to from 10.0 to 13.0, the hydrolytic condensation reaction of the compound selected from the alkoxysilanes and silanol-containing silanes and their partial condensation products is allowed to proceed sufficiently.

No particular limitation is imposed on the acidic substance. Usable examples include acid surfactants such as alkyl sulfates and alkylbenzene sulfonates; carboxylic acids such as formic acid, oxalic acid, malonic acid, lactic acid and malic acid; hydrochloric acid; phosphoric acid; sulfuric acid; methanesulfonic acid; trifluoromethanesulfonic acid; and like.

No particular limitation is imposed on the alkaline substance. Usable examples include alkali metal hydroxides such as potassium hydroxide, sodium hydroxide and lithium hydroxide; alkaline earth metal hydroxides such as calcium hydroxide and barium hydroxide; alkali metal carbonates such as potassium carbonate and sodium carbonate; ammonia; tetraalkylammonium hydroxides such as tetramethylammonium hydroxide and tetraethylammonium hydroxide; amines such as monomethylamine, monoethylamine, monopropylamine, monobutylamine, monopentylamine, dimethylamine, diethylamine, trimethylamine, triethanolamine, and ethyldiamine; and the like.

Among these, ammonia is most suited, because by evaporation, it can be readily eliminated from the resulting powder of fine silicone particles. As ammonia, commercially-available aqua ammonia can be used.

By the catalytic action of the above-described acidic substance or alkaline substance, the alkoxysilanes and silanol-containing silanes and their partial condensation products are allowed to undergo a hydrolytic condensation reaction so that a resinous silicone useful in the present invention is formed. The alkoxysilanes can be represented by the formulas $R^5Si(OR^7)_3$, $R^5_2Si(OR^7)_2$, $R^5_3SiOR^7$ and $Si(OR^7)_4$. In the formulas, each $R^5$ has the same meaning as defined above, and each $R^7$ is an unsubstituted monovalent hydrocarbon group having from 1 to 6 carbon atoms. Examples of $R^7$ include methyl, ethyl, propyl, butyl, pentyl and hexyl. From the standpoint of reactivity, methyl is preferred. Alkoxysilanes: $R^5Si(OR^7)_3$, $R^5_2Si(OR^7)_2$, $R^5_3SiOR^7$ and $Si(OR^7)_4$, will become unit sources for structural units $[R^5SiO_{3/2}]$, $[R^5_2SiO_{2/2}]$, $[R^5_3SiO_{1/2}]$ and $[SiO_{4/2}]$ in a resinous silicone, respectively. The mixing ratio of $R^5Si(OR^7)_3$, $R^5_2Si(OR^7)_2$, $R^5_3SiOR^7$ and $Si(OR^7)_4$ can, therefore, be determined such that the structure of a desired resinous silicone will be given. Their mixing ratio can be set, in terms of molar ratio, at the desired structural units $[R^5SiO_{3/2}]:[R^5_2SiO_{2/2}]:[R^5_3SiO_{1/2}]:[SiO_{4/2}]=R^5Si(OR^7)_3:R^5_2Si(OR^7)_2:R^5_3SiOR^7:Si(OR^7)_4$.

The silanol-containing silanes are compounds having the same formulas as the alkoxysilanes except that $R^7$ is hydrogen. It is only necessary to select one or more compounds from the alkoxysilanes and silanol-containing silanes and their condensation products as desired such that desired structural units will be formed.

While stirring an aqueous dispersion containing at least the core particles, the silicone elastomer and the acidic substance or alkaline substance, the one or more compounds selected from the alkoxysilanes and silanol-containing silanes and their partial condensation products are added thereto and to conduct the hydrolytic condensation reaction. The one or more compounds selected from the alkoxysilanes and silanol-containing silanes and their partial condensation products may be gradually added dropwise, may be added in a form that they are dissolved in water or in a form that they are dispersed in water, or may be added as an admixture with a water-soluble organic solvent such as an alcohol. By the hydrolytic condensation reaction, a silicone resin is formed on the surfaces of the core particles and/or the surfaces of the silicone elastomers, and in addition, adhesion between the core particles and the silicone elastomer takes place to form composite particles with the silicone elastomer adhered on the surfaces of the core particles via the resinous silicone as a binder.

The stirring may preferably be gentle stirring that makes use of a paddle blade, propeller blade, sweptwing blade, anchor blade or the like, because use of vigorous stirring induces aggregation of the particles themselves. However, a stirring intensity sufficient to disperse the one or more compounds selected from the alkoxysilanes and silanol-containing silanes and their partial condensation products in the aqueous dispersion is needed.

When adding to the mixed aqueous dispersion the one or more compounds selected from the alkoxysilanes and silanol-containing silanes and their partial condensation products, the temperature may be preferably from 0 to 60° C., more preferably from 0 to 39° C. If this temperature is lower than 0° C., the aqueous dispersion may potentially solidify. If the temperature is raised higher than 60° C., on the other hand, the resulting particles may potentially undergo aggregation.

For the purpose of allowing the silicone elastomer to adhere evenly to the surfaces of the particles, a water-soluble organic solvent such as an alcohol may be mixed in the aqueous dispersion. To obtain particles surface treated with a silylating agent, treatment may be applied to the finished composite particles. Alternatively, after the one or more compounds selected from the alkoxysilanes and silanol-containing silanes and their partial condensation products are added to the mixed aqueous dispersion, the silylating agent may be added to conduct the surface treatment. Examples of the silylating agent include dimethyldichlorosilane, trimethylchlorosilane, trimethylmethoxysilane, trimethylsilanol-containing silane, hexamethyldisilazane, and the like.

Subsequent to the completion of the addition of the one or more compounds selected from the alkoxysilanes and silanol-containing silanes and their partial condensation products, the stirring may preferably be continued for a while until the hydrolytic condensation reaction comes to completion. To promote the reaction, the reaction system may be heated at from 40 to 100° C., or an acidic substance or alkaline substance may be added further. An alkaline substance or acidic substance may then be charged for neutralization if needed.

Subsequent to the hydrolytic condensation reaction, water is removed. The removal of water can be conducted, for example, by heating the aqueous dispersion under ambient pressure or reduced pressure after the reaction. Specifically, it is possible to mention a method that removes water by allowing the aqueous dispersion to stand under heating after the reaction, a method that removes water by causing the dispersion to flow under heating and stirring, a method that sprays and disperses the dispersion into a stream of hot air as in a spray dryer, a method that makes use of a fluidized heating medium, or a like method. As pre-processing of the above-mentioned operation, the dispersion may be concentrated by a method such as thermal dehydration, filtration separation such as pressure filtration, centrifugal separation, or decantation, and if necessary, the dispersion may be washed with water, an alcohol or the like.

If the powder obtained by removing water from the aqueous dispersion after the reaction is in an aggregated form, it is desired to crush or classify the powder by a crusher such as a jet mill, ball mill or hammer mill.

III. Cosmetic Compositions Containing the Composite Particles

The composite particles (hereinafter referred to as "A") according to the present invention can be used in various cosmetic compositions, and can be suitably used especially in cosmetic compositions applied externally to skin and hair, for example, skin care products, makeup products, hair care products, antiperspirant products, ultraviolet protection products, and the like. The mixing proportion of the composite particles is not limited specifically, and in accordance with each preparation form, can be suitably selected within a range of from 0.1 to 95.0 wt % based on the whole cosmetic composition. In the cosmetic composition, various ingredients employed in the general cosmetic compositions can be mixed to such extents as not to impair the advantageous effects of the present invention. Such ingredients may include, for example, (B) cosmetic oils, (C) water, (D) compounds having alcoholic hydroxyl groups, (E) water-soluble or water-swellable, high molecular compounds, (F) particles other than composite particles according to the present invention, (G) surfactants, (H) compositions composed of crosslinking organopolysiloxanes and cosmetic oils which are liquid at room temperature, (I) silicone resins, (J) silicone waxes, and other additives. They can be used either singly or in combination as desired.

The cosmetic oils (B) may be solid, semi-solid, or liquid. Usable examples include natural, vegetable or animal, oils and fats and semi-synthetic oils and fats, hydrocarbon oils, higher alcohols, ester oils, silicone oils, and fluorine-containing cosmetic oils.

The natural, vegetable or animal, oils and fats and semi-synthetic oils and fats can include avocado oil, linseed oil, almond oil, insect wax, perilla oil, olive oil, cacao butter, kapok wax, kaya (*Torreya nucifera*) oil, carnauba wax, liver oil, candelilla wax, refined candelilla wax, beef tallow, beef foot fat, beef bone fat, hydrogenated beef tallow, kyonin (*Prunus armeniaca*) oil, spermaceti wax, hydrogenated oil, wheat germ oil, sesame oil, rice germ oil, rice bran oil, sugarcane wax, camellia sasanuqua oil, safflower oil, shea butter, Chinese wood oil, cinnamon oil, jojoba wax, squalane, squalene, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape seed oil, bayberry wax, jojoba oil, macadamia nut oil, bees wax, mink oil, meadowfoam oil, cottonseed oil, cotton wax, Japan wax, Rhus Succedanea kernel oil, montan wax, coconut oil, hydrogenated coconut oil, tricoconut oil fatty acid glyceride, mutton tallow, peanut oil, lanolin, liquid lanolin, hydrogenated lanolin, lanolin alcohol, hard lanolin, lanolin acetate, acetylated lanolin alcohol, isopropyl lanolate, polyoxyethylene lanolin alcohol ether, polyoxyethylene lanolin alcohol acetate, lanolin fatty acid polyethylene glycol, polyoxyethylene hydrogenated lanolin alcohol ether, yolk oil, and the like.

The hydrocarbon oils can include linear, branched and volatile hydrocarbon oils, specifically, ozokerite, α-olefin oligomers, light isoparaffins, isododecane, isohexadecane, light liquid isoparaffins, squalane, synthetic squalane, vegetable squalane, squalene, ceresin, paraffins, paraffin wax, polyethylene wax, polyethylene-polypropylene wax, (ethylene/propylene/styrene) copolymer, (butylenes/propylene/styrene) copolymer, liquid paraffins, liquid isoparaffins, pristane, polyisobutylene, hydrogenated polyisobuten, microcrystalline wax, Vaseline, and the like. The higher fatty acids can include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, and the like.

The higher alcohols can include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyl tetradecinol, cholesterol, phytosterol, polyoxyethylene cholesterol ether, monostearyl glycerin ether (batyl alcohol), monooleyl glyceryl ether (selachyl alcohol), and the like.

The ester oils can include diisobutyl adipate, 2-hexyldecyl adipate, di-2-heptylundecyl adipate, N-alkylglycol monoisostearates, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum esters, oleyl oleate, octyldodecyl oleate, decyl oleate, neopentylglycol dioctanoate, neopentylglycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, lauroylsarcosine isopropyl ester, diisostearyl malate, and the like; and glyceride oils such as acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, and diglyceryl myristate isostearate.

The silicone oils can include linear or branched organopolysiloxanes of from low viscosity to high viscosity, such as dimethylpolysiloxane, tristrimethylsiloxymethylsilane, caprylyl methicone, phenyl trimethicone, tetrakis(trimethylsiloxy)silane, methylphenylpolysiloxane, methylhexylpolysiloxane, methylhydrogenpolysiloxane, and dimethylsiloxane-methylphenylsiloxane copolymer; cyclic organopolysiloxanes such as octamethylcyclotetrasiloxane, decamethylcyclopentasiloxane, dodecamethylcyclohexasiloxane, tetramethyltetrahydrogencyclotetrasiloxane, and tetramethyltetraphenylcyclotetrasiloxane; silicone rubbers such as amino-modified organopolysiloxane, pyrrolidone-modified organopolysiloxane, pyrrolidonecarboxylic-acid-modified organopolysiloxane, gummy dimethylpolysiloxane of high polymerization degree, gummy amino-modified organopolysiloxane, and gummy dimethylsiloxane-methylphenylsiloxane copolymer; and cyclic organopolysiloxane solutions of silicone gums or rubber, trimethylsiloxysilicic acid, cyclic siloxanes solution of trimethylsiloxysilicic acid, higher-alkoxy-modified silicones such as stearoxysilicone, silicones modified with higher fatty acids, alkyl-modified silicones, long-chain-alkyl-modified silicones, amino-acid-modified silicones, fluorine-modified silicones, silicone resins, silicone resin solutions, and the like.

The fluorine-containing cosmetic oils can include perfluoropolyether, perfluorodecaline, perfluorooctane, and the like. The amount of the cosmetic oil (B) to be mixed may be selected, dependent on the preparation form, from a range of from 1 to 98 wt % based on the whole cosmetic as desired.

The amount of the water (C) to be mixed may be selected from a range of from 1 to 95 wt % based on the whole cosmetic as desired, although it depends on the preparation form.

The compounds having alcoholic hydroxyl groups (D) can include lower alcohols such as ethanol and isopropanol; and sugar alcohols such as sorbitol and maltose, and can also include sterols such as cholesterol, sitosterol, phytosterol and lanosterol; polyhydric alcohols such as butylene glycol, propylene glycol, dibutylene glycol and pentylene glycol; and the like. Its amount to be mixed may be selected from a range of from 0.1 to 98 wt % based on the whole cosmetic as desired.

The water-soluble or water-swellable, high molecular compounds (E) can include vegetable high-molecular compounds such as gum arabic, tragacanth, galactan, carob gum, guar gum, karaya gum, carrageenan, pectin, agar, quince (marmelo) seed, starch (rice, corn, potato, wheat or the like), algae colloid, tragacanth gum, and locust bean gum; microorganism high-molecular compounds such as xanthan gum, dextran, succinoglucan, and pullulan; animal high-molecular compounds such as collagen, casein, albumin, and gelatin; starch high-molecular compounds such as carboxymethyl starch and methylhydroxypropyl starch; cellulose high-molecular compounds such as methyl cellulose, ethyl cellulose, methylhydroxypropylcellulose, carboxymethylcellulose, hydroxymethylcellulose, hydroxypropylcellulose, nitrocellulose, sodium cellulose sulfate, carboxymethylcellulose sodium, crystalline cellulose, and cellulose powder; alginic acid high-molecular compounds such as sodium alginate and propylene glycol alginate; vinyl high-molecular compounds such as polyvinyl methyl ether and carboxyvinyl polymer; polyoxyethylene high-molecular compounds, polyoxyethylene-polyoxypropylene copolymer high-molecular compound; acrylic high-molecular compounds such as sodium polyacrylate, polyethyl acrylate, polyacrylamide, and acryloyldimethyltaurine salt copolymer; synthetic water-soluble high-molecular compounds such as polyethylenimine and cationic polymer; inorganic water-soluble high-molecular compounds such as bentonite, aluminum magnesium silicate, montmorillonite, beidellite, nontronite, saponite, hectorite, and silicic anhydride; and the like. In these water-soluble high-molecular compounds, film-forming materials such as polyvinyl alcohol and polyvinylpyrrolidone are also included. Its amount to be mixed may preferably be within a range of from 0.1 to 25 wt % based on the whole cosmetic.

The particles (F) other than the composite particles according to the present invention can include inorganic particles, organic particles, composite inorganic/organic particles, silicone resin particles, and the like. As the inorganic particles, resin particles and composite inorganic/organic particles, the same particles and powders as the above-described inorganic particles, resin particles and composite inorganic/organic particles useful in the present invention can be exemplified. The silicone resin particles can include silicone elastomer particles, polymethylsilsesquioxane particles, particles obtained by coating silicone elastomer particles at surfaces thereof with polymethylsilsesquioxane, and the like. As these powders, those obtained by treating their particle surfaces with silylation agents, silicone oils, waxes, paraffins, organic fluorine-containing compounds, surfactants or the like can also be used.

The surfactants (G) can include nonionic, anionic, cationic and amphoteric surfactants, and those similar to the above-described surfactants useful in the production of the composite particles according to the present invention can be exemplified. Among such surfactants, preferred are linear or branched polyoxyethylene-modified organopolysiloxanes, linear or branched polyoxyethylene/polyoxypropylene-modified organopolysiloxanes, linear or branched polyoxyethylene-alkyl co-modified organopolysiloxanes, linear or branched polyoxyethylene/polyoxypropylene-alkyl co-modified organopolysiloxanes, linear or branched polyglycerin-modified organopolysiloxanes, and linear or branched polyglycerin-alkyl co-modified organopolysiloxanes. In these surfactants, preferred are those in which the contents of hydrophilic polyoxyethylene groups, polyoxyethylene/polyoxypropylene groups or polyglycerin residual groups account for from 10 to 70 wt % in their molecules. The amount to be mixed may be in a range of preferably from 0.1 to 20 wt %, more preferably from 0.2 to 10 wt % based on the whole cosmetic. The HLBs of these surfactants may preferably, but are not limited to, from 2 to 14.5.

In the compositions (H) composed of the crosslinking organopolysiloxanes and the cosmetic oils which are liquid at room temperature, the crosslinking organopolysiloxanes may preferably contain the liquid oils as much as or more than their own weights such that they swell with the liquid oils. Usable as the liquid oils can be the liquid silicone oils, hydrocarbon oils, ester oils, natural animal or vegetable oils, semisynthetic oils, and fluorine-containing oils as the ingredient (B). Examples include low-viscosity silicone oils of from 0.65 mm$^2$/s (25° C.) to 100.0 mm$^2$/s (25° C.), hydrocarbon oils such as liquid paraffins, squalane, isododecane and isohexadecane, glyceride oils such as trioctanoine, ester oils such as isotridecyl isononanoate, N-acylglutamate esters and lauroyl sarcosinate esters, natural, animal or vegetable oils such as macadamia nut oil, and the like. Preferably, a crosslinking agent for such a crosslinking organopolysiloxane contains two or more vinylogous reactive sites in its molecule, and reacts with hydrogen atoms bonded directly to silicon atoms and forms a crosslinked structure. Usable as those containing two or more vinylogous reactive sites in their molecules can include organopolysiloxanes containing two or more vinyl groups in their molecules, polyoxyalkylenes containing two or more allyl groups in their molecules, polyglycerins containing two or more allyl groups in their molecules, α,ω-alkenyldienes, and the like. It is also possible to use crosslinking organopolysiloxanes, each of which contains in a crosslinking molecule at least one moiety selected from the group composed of polyoxyalkylene moieties, polyglycerin moieties, long-chain alkyl moieties, alkenyl moieties, aryl moieties, and fluoroalkyl moieties. When a composition composed of a crosslinking organopolysiloxane and a cosmetic oil, which is liquid at room temperature, is used, its mixing amount may be preferably from 0.1 to 80 wt %, more preferably from 1 to 50 wt % based on the whole cosmetic.

The silicone resins (I) may preferably be acryl/silicone, graft or block copolymers as acrylsilicone resins. It is also possible to use acrylsilicone resins, each of which contains in its molecule at least one moiety selected from pyrrolidone moieties, long-chain alkyl moieties, polyoxyalkylene moieties, fluoroalkyl moieties, and anion moieties of carboxylic acids or the like. These silicone resins may preferably be silicone network compounds composed of resins composed of $R^8_3SiO_{0.5}$ units and $SiO_2$ units, resins composed of $R^8_3SiO_{0.5}$ units, $R^8_2SiO$ units and $SiO_2$ units, resins composed of $R^8_3SiO_{0.5}$ units and $R^8SiO_{1.5}$, resins composed of $R^8_3SiO_{0.5}$ units, $R^8_2SiO$ units and $R^8SiO_{1.5}$, and resins composed of $R^8_3SiO_{0.5}$ units, $R^8_2SiO$ units, $R^8SiO_{1.5}$ units and $SiO_2$ units. In these formulas, $R^8$ are each a substituted or unsubstituted, monovalent hydrocarbon group having from 1 to 30 carbon atoms. It is also possible to use silicone network compounds, each of which contains in its molecule at least one moiety selected from pyrrolidone moieties, long-chain alkyl moieties, polyoxyalkylene moieties, polyglycerin moieties, fluoroalkyl moieties, and amino moieties. When a silicone resin such as an acrylsilicone resin or silicone network compound is used, its mixing amount may be preferably from 0.1 to 20 wt %, more preferably from 1 to 10 wt % based on the whole cosmetic.

The silicone waxes (J) may preferably be acryl/silicone, graft or block copolymers as acrylsilicone resins. It is also possible to use acrylsilicone resins, each of which contains in its molecule at least one moiety selected from pyrrolidone moieties, long-chain alkyl moieties, polyoxyalkylene moieties, fluoroalkyl moieties, and anion moieties of carboxylic acids or the like. These silicone waxes can preferably be polylactone-modified polysiloxanes in each of which a 5- or greater-membered, lactone compound binds a polylactone as a ring-opening polymerization product. These silicone waxes can also be silicone-modified olefin waxes, each of which is obtained by subjecting an olefin wax, which has an α-olefin and unsaturated groups formed of a diene, and an organohydrogenpolysiloxane, which has SiH bond(s) as one or more moieties, to an addition reaction. Preferred as the α-olefin in each olefin wax may be one having from 2 to 12 carbon atoms such as ethylene, propylene, 1-butene, 1-hexene or 4-methyl-1-pentene, and preferred as the diene is butadiene, isoprene, 1,4-hexadiene, vinyl norbornene, ethylidene norbornene, dicyclopentadiene, or the like. As the organohydrogenpolysiloxane having SiH bond(s), one of a structure such as a linear or siloxanes-branched structure can be used.

The other additives can include oil-soluble gelling agents, antiperspirants, ultraviolet absorbers, ultraviolet absorbing/scattering agents, humectants, antimicrobial/antiseptic agents, fragrances, salts, antioxidants, pH adjusters, chelating agents, algefacients, antiinflammatories, skin-conditioning ingredients (skin-lightening agents, cellular stimulating agents, skin roughness lessening agents, blood circulation stimulating agents, skin astringents, antiseborrheic agents, etc.), vitamins, amino acids, nucleic acids, hormones, inclusion compounds, hair fixatives, and so on.

The oil-soluble gelling agents can include metallic soaps such as aluminum stearate, magnesium stearate and zinc myristate; amino acid derivatives such as N-lauroyl-L-glutamic acid and α,γ-di-n-butylamine; dextrin fatty acid esters such as dextrin palmitate, dextrin stearate and dextrin 2-ethylhesanoate palmitate; sucrose fatty acid esters such as sucrose palmitate and sucrose stearate; fructooligosaccharide fatty acid esters such as fructooligosaccharide stearate and fructooligosaccharide 2-ethylhexanoate; benzylidene derivatives of sorbitol, such as monobenzylidene sorbitol and dibenzylidene sorbitol; organically-modified clay minerals such as dimethylbenzyldodecylammonium montmorillonite clay and dimethyldioctadecylammonium montmorillonite clay; and the like.

The antiperspirants can include aluminum chlorohydrate, aluminum chloride, aluminum sesquichlorohydrate, zirconyl hydroxychloride, aluminum zirconium hydroxychloride, aluminum zirconium glycine complex, and the like.

The ultraviolet absorbers can include benzoic acid ultraviolet absorbers such as paraminobenzoic acid; anthranilic acid ultraviolet absorbers such as methyl anthranilate; salicylic acid ultraviolet absorbers such as methyl salicylate, octyl salicylate and trimethylcyclohexyl salicylate; cinnamic acid ultraviolet absorbers such as octyl paramethoxycinnamate; benzophenone ultraviolet absorbers such as 2,4-dihydroxybenzophenone; urocanic acid ultraviolet absorbers such as ethyl urocanate; dibenzoylmethane ultraviolet absorbers such as 4-t-butyl-4'-methoxy-dibenzoylmethane; phenylbenzimidazolesulfonic acid, and triazine derivatives; and the like. The ultraviolet absorbing/scattering agents can include particles capable of absorbing and scattering ultraviolet rays, such as fine particulate titanium oxide, fine particulate iron-containing titanium oxide, fine particulate zinc oxide, fine particulate cerium oxide, and complexes thereof. It is also possible to use dispersions in which these UV-absorbing/scattering particles have been dispersed beforehand in cosmetic oils.

The humectants can include glycerin, sorbitol, propylene glycol, dipropylene glycol, 1,3-butylene glycol, pentylene glycol, glucose, xylitol, maltitol, polyethylene glycol, hyaluronic acid, condroitin sulfate, pyrrolidone carboxylate salts, polyoxyethylene methyl glucoside, polyoxypropylene methyl glucoside, egg-yolk lecithin, soybean lecithin, phosphatidylcholine, phosphatidylethanolamine, phosphatidylserine, phosphatidylglycerol, phosphatidylinositol, phosphosphingolipid, and the like.

The antimicrobial/antiseptic agents can include alkyl paraoxybenzoates, benzoic acid, sodium benzoate, sorbic acid, potassium sorbate, phenoxyethanol, and the like. Antibacterial agents can include benzoic acid, salicylic acid, phenolic acid, sorbic acid, alkyl paraoxybenzoates, parachlorometacresol, hexachlorophene, benzalkonium chloride, chlorohexidine chloride, trichlorocarbanilide, photosensitizing dyes, phenoxyethanol, and the like.

The salts can include inorganic salts, organic acid salts, amine salts, and amino acid salts. Examples of the inorganic salts include the sodium salts, potassium salts, magnesium salts, calcium salts, aluminum salts, zirconium salts, zinc salts and the like of inorganic acids such as hydrochloric acid, sulfuric acid, carbonic acid and nitric acid; examples of the organic acid salts include salts of organic acids such as acetic acid, dehydroacetic acid, citric acid, malic acid, succinic acid, ascorbic acid and stearic acid; and examples of the amine salts and amino acid salts include salts of amines such as triethanolamine, salts of amino acids such as glutamic acid, and the like. Also usable are salts of hyaluronic acid, condroitin sulfuric acid and the like, aluminum zirconium glycine complex and the like, and acid-alkali neutralization salts and the like useful in cosmetic formulas.

The antioxidants can include tocopherol, p-t-butylphenol, butylhydroxyanisole, dibutylhydroxytoluene, phytic acid, and the like. The pH adjusters can include lactic acid, citric acid, glycolic acid, succinic acid, tartaric acid, dl-malic acid, potassium carbonate, sodium hydrogencarbonate, ammonium hydrogencarbonate, and the like. The chelating agents can include alanine, sodium edetate, sodium polyphosphate, sodium metaphosphate, phosphoric acid, and the like. The algefacients can include L-menthol, camphor, and the like. The antiinflammatories can include allantoin, glycyrrhizic acid and its salts, glytylretinic acid and stearyl glytylretinate, tranexamic acid, azulene, and the like.

The skin-conditioning ingredients can include skin-lightening agents such as placenta extract, arbutin, glutathione and saxifrage extract; cellular stimulating agents such as royal jelly, photosensitizing dyes, cholesterol derivatives, calf blood extract and the like; skin roughness lessening agents; blood circulation stimulating agents such as nonylic acid vanillylamide, benzyl nicotinate, β-butoxyethyl nicotinate, capsaicin, zingerone, cantharis tincture, ichthammol, caffeine, tannic acid, α-borneol, tocopherol nicotinate, inositol hexanicotinate, cyclandelate, cinnarizine, tolazoline, acetylcholine, varapamil, cepharanthine and γ-orizanol; skin astringents such as zinc oxide and tannic acid; antiseborrheic agents such as sulfur and thianthrol; and the like.

The vitamins include vitamin A and its analogs, such as vitamin A oil, retinol, retinol acetate and retinol palmitate; vitamin B and its analogs, e.g., vitamin $B_2$ and its analogs such as riboflavin, riboflavin butyrate and flavin adenine nucleotide, vitamin $B_6$ and its analogs such as pyridoxine hydrochloride, pyridoxine dioctanoate and pyridoxine tripalmitate, vitamin $B_{12}$ and its derivatives, and vitamin $B_{15}$ and its derivatives; vitamin C and its analogs such as L-ascorbic acid, L-ascorbate dipalmitate esters, L-ascorbic acid-2-sodium sulfate and dipotassium L-ascorbate phosphate; vitamin D and its analogs such as ergocalciferol and cholecalciferol; vitamin E and its analogs such as α-tocopherol, β-tocopherol, γ-tocopherol, dl-α-tocopherol acetate, dl-α-tocopherol nicotinate and dl-α-tocopherol succinate; and nicotinic acid and its derivatives such as nicotinic acid, benzyl nicotinate and nicotinic acid amide; vitamin H, vitamin P, pantothenic acid and its derivatives such as calcium pantothenate, D-pantothenyl alcohol, pantothenyl ethyl ether and acetylpantothenyl ethyl ether, biotin, and the like.

The amino acids can include glycine, valine, leucine, isoleucine, serine, threonine, phenylalanine, arginine, lysine, aspartic acid, glutamic acid, cystine, cysteine, methionine, tryptophan, and the like. The nucleic acids can include deoxyribonucleic acid and the like. The hormones can include estradiol, ethenyl estradiol, and the like.

The hair fixatives can include amphoteric, anionic, cationic or nonionic high-molecular compounds. Suitably usable examples include polyvinylpyrrolidone high-molecular compounds such as polyvinylpyrrolidone and polyvinylpyrrolidone/vinyl acetate copolymer, acidic vinyl ether high-molecular compounds such as methyl vinyl ether/maleic anhydride alkyl half ester copolymer, acetic polyvinyl acetate high-molecular compounds such as vinyl acetate/crotonic acid copolymer, acidic acrylic high-molecular compounds such as (meth)acrylic acid/alkyl (meth)acrylate copolymer and (meth)acrylic acid/alkyl (meth)acrylate/alkylacrylamide copolymer, and amphoteric acrylic high-molecular compounds such as N-methacryloylethyl-N,N-dimethylammonium.α-N-methylcarboxy-betaine/alkyl (meth)acrylate copolymer and hydroxypropyl (meth)acrylate/butylaminoethyl methacrylate/acrylic acid octylamide copolymer. Further, naturally-derived high-molecular compounds such as cellulose and its derivatives and keratin or collagen and its derivatives can also be used suitably.

The cosmetic composition according to the present invention can be in the form of a powder, an oil, a water-in-oil emulsion, an oil-in-water emulsion, a non-aqueous emulsion, a multiple emulsion such as W/O/W or O/W/O, or the like, or can be in a liquid form, milk lotion form, cream form, solid form, paste form, gel form, powder form, press cake form, multilayer form, mousse form, spray form, stick form, pencil form, or the like. Examples of the cosmetic include skin care cosmetics such as lotions, milk lotions, creams, cleansings, packs, oil liquids, massage aids, beauty liquids, beauty oils, cleansing products, deodorants, hand creams, lip creams, and wrinkle concealers; makeup cosmetics such as makeup foundations, concealers, face powders, powder foundations, liquid foundations, cream foundations, oil foundations, rouges, eye shadows, mascaras, eyeliners, eyebrow pencils, and lipsticks; hair cosmetics such as shampoos, hair rinses, hair conditioners and hair wave sets; antiperspirants; ultraviolet protection cosmetics such as sunscreen oils, sunscreen lotions and sunscreen creams.

As the preparation forms of these cosmetic compositions, various forms can be chosen including liquid forms, milk lotion forms, cream forms, solid forms, paste forms, gel forms, powder forms, press cake forms, multilayer forms, mousse forms, spray forms, stick forms and pencil forms.

EXAMPLES

Examples and Comparative Examples will hereinafter be presented to specifically describe the present invention, although the present invention shall not be limited to or by the following examples. It is to be noted that in the examples, each viscosity is a value as measured at 25° C. and each "%" designating a concentration or content indicates "wt %."

Preparation Example 1

Methylvinylpolysiloxane represented by the below-described formula (1) and having a viscosity of 580 mm$^2$/s (450 g) and methylhydrogenpolysiloxane represented by the below-described formula (2) and having a viscosity of 30 mm$^2$/s (18 g, which was a mixing amount to give 1.1 hydrosilyl groups per vinyl group) were charged in a glass beaker of 1 liter capacity, and were mixed into a solution by using a homomixer. Polyoxyethylene lauryl ether ("EMULGEN 109P," trade name; product of Kao Corporation) (22 g) and water (45 g) were added. When stirred by using the homomixer, the mixture was increased in viscosity to a state that stirring was no longer feasible. Using a homodisper, the thickened mixture was kneaded for 15 minutes. Water (463 g) was then added, and mixing was conducted by using the homomixer. As a result, a homogeneous white emulsion was obtained. The emulsion was transferred into a glass flask of 1 liter capacity, which was equipped with a stirrer having an anchor-shaped stirring blade. After the temperature was controlled to 15 to 20° C., a mixed solution of a solution of a chloroplatinic acid-olefin complex in toluene (platinum content: 0.5%) (0.7 g) and polyoxyethylene lauryl ether ("EMULGEN 109P," trade name; product of Kao Corporation) (1.4 g) was added under stirring, followed by stirring at the same temperature for 24 hours to obtain an aqueous dispersion of a silicone elastomer. The thus-obtained aqueous dispersion of the silicone elastomer will be referred to as "Aqueous Silicone Elastomer Dispersion-1."

The volume average particle size of the silicone elastomer was measured by using a "LASER DIFFRACTION/SCATTERING PARTICLE SIZE DISTRIBUTION ANALYZER LA-920" (manufactured by Horiba, Ltd.). As a result, the volume average particle size was found to be 460 nm. Methylvinylpolysiloxane represented by the formula (1) and having the viscosity of 580 mm$^2$/s, methylhydrogenpolysiloxane represented by the formula (2) and having the viscosity of 30 mm$^2$/s, and a solution of the chloroplatinic acid-olefin complex in toluene (platinum content: 0.5%) were mixed at the above-described mixing ratio, and the resulting mixture was poured into an aluminum Petri dish to give a thickness of 10 mm. After allowed to stand at 25° C. for six hours, the mixture was then heated for one hour in a constant-temperature chamber controlled at 50° C. The resulting cured product was a non-tacky rubber elastomer. Its hardness was measured by a durometer A hardness meter. As a result, the hardness was found to be 29.

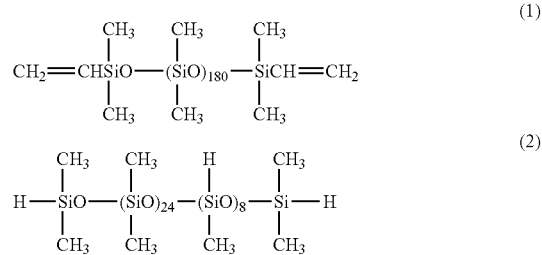

Preparation Example 2

Preparation of Aqueous Dispersion of Silicone Elastomer

Methylvinylpolysiloxane represented by the below-described formula (3) and having a viscosity of 4,900 mm$^2$/s (400 g) and methylhydrogenpolysiloxane represented by the above-described formula (2) and having the viscosity of 30 mm$^2$/s (7 g, which was a mixing amount to give 1.1 hydrosilyl groups per vinyl group) were charged in a glass beaker of 1 liter capacity, and were mixed into a solution by using a homomixer. Polyoxyethylene lauryl ether ("EMULGEN 109P," trade name; product of Kao Corporation) (62 g) and water (35 g) were added. When stirred by using the homomixer, the mixture was increased in viscosity to a state that stirring was no longer feasible. Using a homodisper, the thickened mixture was kneaded for 15 minutes. Water (494 g) was then added, and mixing was conducted by using the homomixer. As a result, a homogeneous white emulsion was obtained. The emulsion was transferred into a glass flask of 1 liter capacity, which was equipped with a stirrer having an anchor-shaped stirring blade. After the temperature was controlled to 15 to 20° C., a mixed solution of a solution of the chloroplatinic acid-olefin complex in toluene (platinum content: 0.5%) (0.6 g) and polyoxyethylene lauryl ether ("EMULGEN 109P," trade name; product of Kao Corporation) (1.2 g) was added under stirring, followed by stirring at the same temperature for 24 hours to obtain an aqueous dispersion of a silicone elastomer. The thus-obtained aqueous dispersion of the silicone elastomer will be referred to as "Aqueous Silicone Elastomer Dispersion-2."

The volume average particle size of the silicone elastomer was measured by using the "LASER DIFFRACTION/SCATTERING PARTICLE SIZE DISTRIBUTION ANALYZER LA-920" (manufactured by Horiba, Ltd.). As a result, the volume average particle size was found to be 190 nm. Methylvinylpolysiloxane represented by the below-described formula (3) and having a viscosity of 4,900 mm$^2$/s, methylhydrogenpolysiloxane represented by the above-described formula (2) and having the viscosity of 30 mm$^2$/s, and a solution of the chloroplatinic acid-olefin complex in toluene (platinum content: 0.5%) were mixed at the above-described mixing ratio, and the resulting mixture was poured into an aluminum Petri dish to give a thickness of 10 mm. After allowed to stand at 25° C. for six hours, the mixture was then heated for one hour in the constant-temperature chamber controlled at 50° C. The resulting cured product was a non-tacky rubber elastomer. Its hardness was measured by the durometer A hardness meter. As a result, the hardness was found to be 20.

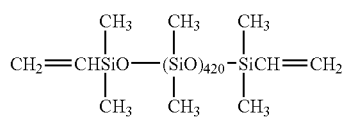
(3)

Preparation Example 3

Preparation of Aqueous Dispersion of Silicone Elastomer

Methylvinylpolysiloxane represented by the above-described formula (3) and having the viscosity of 4,900 mm$^2$/s (340 g) and methylhydrogenpolysiloxane represented by the below-described formula (4) and having a viscosity of 410 mm$^2$/s (68 g, which was a mixing amount to give 1.1 hydrosilyl groups per vinyl group) were charged in a glass beaker of 1 liter capacity, and were mixed into a solution by using a homomixer. Polyoxyethylene lauryl ether ("EMULGEN 109P," trade name; product of Kao Corporation) (62 g) and water (35 g) were added. When stirred by using the homomixer, the mixture was increased in viscosity to a state that stirring was no longer feasible. Using a homodisper, the thickened mixture was kneaded for 15 minutes. Water (493 g) was then added, and mixing was conducted by using the homomixer. As a result, a homogeneous white emulsion was obtained. The emulsion was transferred into a glass flask of 1 liter capacity, which was equipped with a stirrer having an anchor-shaped stirring blade. After the temperature was controlled to 15 to 20° C., a mixed solution of a solution of the chloroplatinic acid-olefin complex in toluene (platinum content: 0.5%) (0.6 g) and polyoxyethylene lauryl ether ("EMULGEN 109P," trade name; product of Kao Corporation) (1.2 g) was added under stirring, followed by stirring at the same temperature for 24 hours to obtain an aqueous dispersion of a silicone elastomer. The thus-obtained aqueous dispersion of the silicone elastomer will be referred to as "Aqueous Silicone Elastomer Dispersion-3."

The volume average particle size of the silicone elastomer was measured by using the "LASER DIFFRACTION/SCATTERING PARTICLE SIZE DISTRIBUTION ANALYZER LA-920" (manufactured by Horiba, Ltd.). As a result, the volume average particle size was found to be 200 nm. Methylvinylpolysiloxane represented by the above-described formula (3) and having the viscosity of 4,900 mm$^2$/s, methylhydrogenpolysiloxane represented by the below-described formula (4) and having the viscosity of 410 mm$^2$/s, and a solution of the chloroplatinic acid-olefin complex in toluene (platinum content: 0.5%) were mixed at the above-described mixing ratio, and the resulting mixture was poured into an aluminum Petri dish to give a thickness of 10 mm. After allowed to stand at 25° C. for six hours, the mixture was then heated for one hour in the constant-temperature chamber controlled at 50° C. The resulting cured product was a slightly tacky rubber elastomer. Its hardness was measured by the durometer A hardness meter. As a result, the hardness was found to be 12.

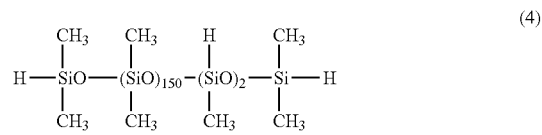
(4)

Preparation Example 4

Preparation of Aqueous Dispersion of Silicone Elastomer

Methylvinylpolysiloxane represented by the below-described formula (5) and having a viscosity of 10 mm$^2$/s (94 g) and organohydrogenpolysiloxane represented by the below-described formula (6) and having a viscosity of 110 mm$^2$/s (360 g, which was a mixing amount to give 1.1 hydrosilyl groups per vinyl group) were charged in a glass beaker of 1 liter capacity, and were mixed into a solution by using a homomixer. Polyoxyethylene lauryl ether ("EMULGEN 109P," trade name; product of Kao Corporation) (45 g) and water (100 g) were added. When stirred by using the homomixer, an increase in viscosity was recognized. The mixture was stirred further for 15 minutes. After water (398 g) was added to form a homogeneous solution, the solution was caused to pass under a pressure of 30 MPa through a homogenizer to obtain a white emulsion. The emulsion was transferred into a glass flask of 1 liter capacity, which was equipped with a stirrer having an anchor-shaped stirring blade. After the temperature was controlled to 15 to 20° C., a mixed solution of a solution of the chloroplatinic acid-olefin complex in toluene (platinum content: 0.5%) (1.4 g) and polyoxyethylene lauryl ether ("EMULGEN 109P," trade name; product of Kao Corporation) (1.4 g) was added under stirring, followed by stirring at from 35 to 45° C. for five hours to obtain an aqueous dispersion of a silicone elastomer. The thus-obtained aqueous dispersion of the silicone elastomer will be referred to as "Aqueous Silicone Elastomer Dispersion-4."

The volume average particle size of the silicone elastomer was measured by using the "LASER DIFFRACTION/SCATTERING PARTICLE SIZE DISTRIBUTION ANALYZER LA-920" (manufactured by Horiba, Ltd.). As a result, the volume average particle size was found to be 190 nm. Methylvinylpolysiloxane represented by the above-described formula (5) and having the viscosity of 10 mm$^2$/s, organohydrogenpolysiloxane represented by the below-described formula (6) and having the viscosity of 110 mm$^2$/s, and a solution of the chloroplatinic acid-olefin complex in toluene (platinum content: 0.5%) were mixed at the above-described mixing ratio, and the resulting mixture was poured into an aluminum Petri dish to give a thickness of 10 mm. After allowed to stand at 25° C. for six hours, the mixture was then heated for one hour in the constant-temperature chamber controlled at 50° C. The resulting cured product was a non-tacky rubber elastomer. Its hardness was measured by the durometer E hardness meter. As a result, the hardness was found to be 44.

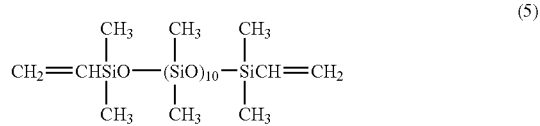

(5)

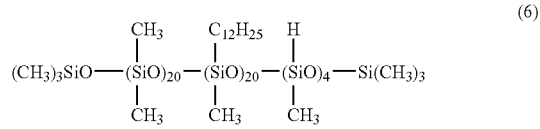

(6)

Example 1

In a glass flask of 3 liter capacity equipped with a stirrer having an anchor-shaped stirring blade, barium sulfate particles ("PLATELET BARIUM SULFATE HL," trade name; product of Sakai Chemical Industry Co., Ltd.; shape: plate, average particle size: 15 μm) (180 g), Aqueous Silicone Elastomer Dispersion-1 (26 g; an amount to give 6.8 parts by weight of the silicone elastomer per 100 parts by weight of the barium sulfate particles), a 30% aqueous solution of dodecyltrimethylammonium chloride ("CATION BB," trade name, product of NOF Corporation) (5 g), 28% aqueous ammonia (29 g) and water (1,233 g) were charged. The pH of the resulting solution at that stage was 11.3. After the temperature was controlled to 5 to 10° C., methyltrimethoxysilane (27 g; an amount to give 109 parts by weight of a silicone resin after a hydrolytic condensation reaction per 100 parts by weight of the silicone elastomer) was added dropwise over 20 minutes. During the dropwise addition, the liquid temperature was maintained at 5 to 10° C. The resulting mixture was stirred further for one hour. The mixture was then heated to 55 to 60° C. and, while maintaining that temperature, stirring was conducted for one hour to bring the hydrolytic condensation reaction of methyltrimethoxysilane to completion. The resultant suspension was dehydrated by using a press filter.

The dehydration product was transferred into a glass flask of 3 liter capacity equipped with a stirrer having an anchor-shaped stirring blade. Water (1,000 g) was added. After stirring was conducted for 30 minutes, dehydration was conducted by using the press filter. The dehydration product was again transferred into a glass flask. The glass flask was immersed in an oil bath controlled at 110° C., and drying was conducted with stirring to obtain particles having fluidity.

The thus-obtained particles were observed under an electron microscope. As a result, it was confirmed that spherical particles of about 500 nm adhered on surfaces of plate particles to form composite particles with the silicone elastomer adhered on the surfaces of the barium sulfate particles. It was also found that a resinous silicone served as a binder to keep the silicone elastomer adherent to the barium sulfate particles. Namely, without the binder that serves to keep the silicone elastomer adherent to the surfaces of the barium sulfate particles, the silicone elastomer is presumed to fall off from the surfaces of the barium sulfate particles through operations such as the above-described water washing and drying even if the silicone elastomer has adhered on the surfaces of the barium sulfate particles. If the silicone elastomer falls off, the aggregation of the particles themselves is considered to occur as the silicone elastomer has high cohesive property. Particles of such a shape were, however, not observed under the electron microscope.

Further, polyoxyethylene lauryl ether ("EMULGEN 109 P," trade name; product of Kao Corporation) (0.2 g), water (50 g) and the composite particles (2.5 g) were weighed in a 100-mL glass bottle. After shaken for 30 minutes, the resulting mixture was allowed to stand for 24 hours to observe the particles as to whether they came to the surface or they settled. If the silicone elastomer falls off from the surfaces of the barium sulfate particles, the silicone elastomer comes to the surface because its specific gravity is smaller than water. The silicone elastomer, however, settled in its entirety. This result also suggests that the silicone resin serves as a binder to keep the silicone elastomer adherent to the barium sulfate particles.

Example 2

In a glass flask of 3 liter capacity equipped with a stirrer having an anchor-shaped stirring blade, sericite ("SANSHIN MICA FSE," trade name; product of Sanshin Mining Ind. Co., Ltd.; shape: plate, average particle size: 10 μm) (150 g), Aqueous Silicone Elastomer Dispersion-2 (41 g; an amount to give 11.1 parts by weight of the silicone elastomer per 100 parts by weight of sericite), 28% aqueous ammonia (30 g) and water (1,238 g) were charged. The pH of the resulting solution at that stage was 11.3. After the temperature was controlled to 5 to 10° C., a mixed solution of methyltrimethoxysilane (40 g) and γ-aminopropyltrimethoxysilane (1 g) (an amount to give 122 parts by weight of a silicone resin after a hydrolytic condensation reaction per 100 parts by weight of the silicone elastomer) was added dropwise over 25 minutes. During the dropwise addition, the liquid temperature was maintained at 5 to 10° C. The resulting mixture was stirred further for one hour. The mixture was then heated to 55 to 60° C. and, while maintaining that temperature, stirring was conducted for one hour to bring the hydrolytic condensation reaction of methyltrimethoxysilane and γ-aminopropyltrimethoxysilane to completion. The resultant suspension was dehydrated by using a press filter. The dehydration product was transferred into a glass flask of 3 liter capacity equipped with a stirrer having an anchor-shaped stirring blade. Water (1,000 g) was added. After stirring was conducted for 30 minutes, dehydration was conducted by using the press filter. The dehydration product was again transferred into a glass flask. The glass flask was immersed in an oil bath controlled at 110° C., and drying was conducted with stirring to obtain particles having fluidity.

The thus-obtained particles were observed under the electron microscope. As a result, it was confirmed that spherical particles of about 200 nm adhered on surfaces of plate particles to form composite particles with the silicone elastomer adhered on the surfaces of the sericite particles. It was also found that the silicone resin served as a binder to keep the silicone elastomer adherent to sericite.

Further, polyoxyethylene lauryl ether ("EMULGEN 109 P," trade name; product of Kao Corporation) (0.2 g), water (50 g) and the composite particles (2.5 g) were weighed in a 100-mL glass bottle. After shaken for 30 minutes, the resulting mixture was allowed to stand for 24 hours to observe the particles as to whether they came to the surface or they settled. If the silicone elastomer falls off from sericite sulfate, the silicone elastomer comes to the surface because its specific gravity is smaller than water. The silicone elastomer, however, settled in its entirety. This result also suggests that the silicone resin serves as a binder to keep the silicone elastomer adherent to sericite.

Example 3

In a glass flask of 3 liter capacity equipped with a stirrer having an anchor-shaped stirring blade, hydrated silicon dioxide particles ("SIL-LEAF," trade name; product of Mizusawa Industrial Chemicals, Inc.; shape: plate, average particle size: 6 μm, water content: 8%) (163 g), Aqueous Silicone Elastomer Dispersion-2 (33 g; an amount to give 9.0 parts by weight of the silicone elastomer per 100 parts by weight of silicon dioxide particles), a 30% aqueous solution of dodecyltrimethylammonium chloride ("CATION BB," trade name, product of NOF Corporation) (4 g), 28% aqueous ammonia (30 g) and water (1,241 g) were charged. The pH of the resulting solution at that stage was 11.3. After the temperature was controlled to 5 to 10° C., a mixed solution of methyltrimethoxysilane (24 g) and dimethyldimethoxysilane (5 g) (an amount to give 111 parts by weight of a silicone resin after a hydrolytic condensation reaction per 100 parts by weight of the silicone elastomer) was added dropwise over 20 minutes. During the dropwise addition, the liquid temperature was maintained at 5 to 10° C. The resulting mixture was stirred further for one hour. The mixture was then heated to 55 to 60° C. and, while maintaining that temperature, stirring was conducted for one hour to bring the hydrolytic condensation reaction of methyltrimethoxysilane and dimethyldimethoxysilane to completion. The resultant suspension was dehydrated by using a press filter. The dehydration product was transferred into a glass flask of 3 liter capacity equipped with a stirrer having an anchor-shaped stirring blade. Water (1,000 g) was added. After stirring was conducted for 30 minutes, dehydration was conducted by using the press filter. The dehydration product was again transferred into a glass flask. The glass flask was immersed in an oil bath controlled at 110° C., and drying was conducted with stirring to obtain particles having fluidity.

The thus-obtained particles were observed under the electron microscope. As a result, it was confirmed that spherical particles of about 200 nm adhered on surfaces of plate particles to form composite particles with the silicone elastomer adhered on the surfaces of the silicon dioxide particles. It was also found that the silicone resin served as a binder to keep the silicone elastomer adherent to the silicon dioxide particles.

Further, polyoxyethylene lauryl ether ("EMULGEN 109 P," trade name; product of Kao Corporation) (0.2 g), water (50 g) and the composite particles (2.5 g) were weighed in a 100-mL glass bottle. After shaken for 30 minutes, the resulting mixture was allowed to stand for 24 hours to observe the particles as to whether they came to the surface or they settled. If the silicone elastomer falls off from the surfaces of silicon dioxide particles, the silicone elastomer comes to the surface because its specific gravity is smaller than water. The silicone elastomer, however, settled in its entirety. This result also suggests that the silicone resin serves as a binder to keep the silicone elastomer adherent to silicon dioxide particles.

Example 4

In a glass flask of 3 liter capacity equipped with a stirrer having an anchor-shaped stirring blade, calcium carbonate particles ("WHISCAL A," trade name; product of Maruo Calcium Co., Ltd.; shape: needle, average particle size (major diameter): 25 μm) (225 g), Aqueous Silicone Elastomer Dispersion-3 (24 g; an amount to give 4.4 parts by weight of the silicone elastomer per 100 parts by weight of the calcium carbonate particles), sodium lauryl sulfate ("NIKKOL SLS," trade name, product of Nikko Chemicals Co., Ltd.) (1 g), 28% aqueous ammonia (29 g) and water (1,241 g) were charged. The pH of the resulting solution at that stage was 11.3. After the temperature was controlled to 5 to 10° C., methyltrimethoxysilane (27 g; an amount to give 136 parts by weight of a resinous silicone after a hydrolytic condensation reaction per 100 parts by weight of the silicone elastomer) was added dropwise over 20 minutes. During the dropwise addition, the liquid temperature was maintained at 5 to 10° C. The resulting mixture was stirred further for one hour. The mixture was then heated to 55 to 60° C. and, while maintaining that temperature, stirring was conducted for one hour to bring the hydrolytic condensation reaction of methyltrimethoxysilane to completion. The resultant suspension was dehydrated by using a press filter. The dehydration product was transferred into a glass flask of 3 liter capacity equipped with a stirrer having an anchor-shaped stirring blade. Water (1,000 g) was added. After stirring was conducted for 30 minutes, dehydration was conducted by using the press filter. The dehydration product was again transferred into a glass flask. The glass flask was immersed in an oil bath controlled at 110° C., and drying was conducted with stirring to obtain particles having fluidity.

The thus-obtained particles were observed under the electron microscope. As a result, it was confirmed that spherical particles of about 200 nm adhered on surfaces of needle particles to form composite particles with the silicone elastomer adhered on the surfaces of the calcium carbonate particles. It was also found that the silicone resin served as a binder to keep the silicone elastomer adherent to the calcium carbonate particles.

Further, polyoxyethylene lauryl ether ("EMULGEN 109 P," trade name; product of Kao Corporation) (0.2 g), water (50 g) and the composite particles (2.5 g) were weighed in a 100-mL glass bottle. After shaken for 30 minutes, the resulting mixture was allowed to stand for 24 hours to observe the particles as to whether they came to the surface or they settled. If the silicone elastomer falls off from the surfaces of calcium carbonate particles, the silicone elastomer comes to the surface because its specific gravity is smaller than water. The silicone elastomer, however, settled in its entirety. This result also suggests that the silicone resin serves as a binder to keep the silicone elastomer adherent to the calcium carbonate particles.

Example 5

In a glass flask of 3 liter capacity equipped with a stirrer having an anchor-shaped stirring blade, crosslinked spherical methyl methacrylate ("GANZ PEARL GMX-0810," trade name; product of Ganz Chemical Co., Ltd.; shape: sphere, average particle size: 8 µm) (120 g), Aqueous Silicone Elastomer Dispersion-4 (30 g; an amount to give 11.4 parts by weight of the silicone elastomer per 100 parts by weight of the crosslinked spherical methyl methacrylate particles), 28% aqueous ammonia (30 g) and water (1,282 g) were charged. The pH of the resulting solution at that stage was 11.3. After the temperature was controlled to 5 to 10° C., a mixed solution of methyltrimethoxysilane (37 g) and γ-aminopropyltrimethoxysilane (1 g) (an amount to give 138 parts by weight of a silicone resin after a hydrolytic condensation reaction per 100 parts by weight of the silicone elastomer) was added dropwise over 25 minutes. During the dropwise addition, the liquid temperature was maintained at 5 to 10° C. The resulting mixture was stirred further for one hour. The mixture was then heated to 55 to 60° C. and, while maintaining that temperature, stirring was conducted for one hour to bring the hydrolytic condensation reaction of methyltrimethoxysilane and γ-aminopropyltrimethoxysilane to completion. The resultant suspension was dehydrated by using a press filter. The dehydration product was transferred into a glass flask of 3 liter capacity equipped with a stirrer having an anchor-shaped stirring blade. Water (1,000 g) was added. After stirring was conducted for 30 minutes, dehydration was conducted by using the press filter. The dehydration product was again transferred into a glass flask. The glass flask was immersed in an oil bath controlled at 110° C., and drying was conducted with stirring to obtain particles having fluidity.

The thus-obtained particles were observed under the electron microscope. As a result, it was confirmed that spherical particles of about 200 nm adhered on surfaces of spherical particles to form composite particles with the silicone elastomer adhered on the surfaces of the crosslinked spherical methyl polymethacrylate particles. It was also found that the silicone resin served as a binder to keep the silicone elastomer adherent to the crosslinked spherical methyl polymethacrylate particles.

Further, polyoxyethylene lauryl ether ("EMULGEN 109 P," trade name; product of Kao Corporation) (0.2 g), water (50 g) and the composite particles (2.5 g) were weighed in a 100-mL glass bottle. After shaken for 30 minutes, the resulting mixture was allowed to stand for 24 hours to observe the particles as to whether they came to the surface or they settled. If the silicone elastomer falls off from the surfaces of crosslinked spherical methyl polymethacrylate particles, the silicone elastomer comes to the surface because its specific gravity is smaller than water. The silicone elastomer, however, settled in its entirety. This result also suggests that the silicone resin serves as a binder to keep the silicone elastomer adherent to crosslinked spherical methyl polymethacrylate particles.

Comparative Example 1

Barium sulfate particles: Barium sulfate particles used in Example 1 were used as they were.

Comparative Example 2

Powder treated with metallic soap: Sericite (98 parts by weight) used in Example 2 was suspended in water (400 parts by weight). Sodium stearate (3.5 parts by weight) was added, followed by thorough stirring at 60° C. To the resulting mixture, a 20% solution of aluminum sulfate was added dropwise over 10 minutes, followed by stirring for 10 minutes. The thus-prepared mixture was dehydrated by a suction filter, and then dried at 110° C. for 12 hours to obtain sericite treated with a metallic soap.

Comparative Example 3

Powder treated with methylhydrogensiloxane: Hydrated silicon dioxide particles (95 parts by weight) used in Example 3 was charged in a reactor. While gradually adding to the particles a solution of methylhydrogenpolysiloxane (five parts) diluted in toluene, stirring was conducted. The resulting mixture was heated to distill off toluene. Stirring was conducted at 150° C. for three hours to perform baking treatment so that silicon dioxide treated with methylhydrogenpolysiloxane was obtained.

Comparative Example 4

Calcium carbonate particles: Calcium carbonate particles used in Example 4 were used as they were.

Comparative Example 5

Crosslinked spherical methyl polymethacrylate: Crosslinked spherical methyl polymethacrylate particles used in Example 5 was used as it was.

[Assessment of Composite Particles]

The composite particles obtained in the examples and the powders of the comparative examples were each assessed by a panel of 10 expert assessors for spreadability (flatting property), softness (touch feel), adhesion (adherence, evenness), powder dispersibility, skin configuration correcting effect (soft focus effect) upon application of a corresponding simple powder mixture formulated as will be described below. The results are shown in Table 2.

(Formula)

| Simple powder mixture | (parts by weight) |
|---|---|
| Particles (powder) | 4 parts |
| Untreated talc | 92 parts |
| Dimethylpolysiloxane (6 mm$^2$/s (25° C.) | 2 parts |
| Squalane | 2 parts |
| Total | 100 parts |

* The particles of Examples 1 to 5 and Comparative Examples 1 to 5

(Making Method)

In the formula of simple powder mixture, the powder ingredients were weighed, respectively, and were stirred for one minute by a high-speed blender. To the resulting powder mixture, the oil-phase ingredients were added. After stirring was conducted for six minutes, the resulting mixture was caused to pass through a 100-mesh filter, thereby obtaining the simple powder mixture.

(Assessment)

The spreadability (flatting property), softness (touch feel), adhesion (adherence, evenness), powder mixing state (dispersibility), skin configuration correcting effect (soft focus effect) upon application of simple powder mixture were assessed in accordance with the assessment standards shown in Table 1. Based on the average scores by the 10 expert assessors, the results were ranked in accordance with the below-described ranking standards.

TABLE 1

Assessment standards

| Scores | Spreadability | Softness | Adhesion | Mixing state | Skin configuration correcting effect (soft focus effect) |
|---|---|---|---|---|---|
| 5 | Good | Good | None | Good | Good |
| 4 | Slightly good | Slightly good | Substantially none | Slightly good | Slightly good |
| 3 | Moderate | Moderate | Moderate | Moderate | Moderate |
| 2 | Slightly poor | Slightly poor | Not satisfactory | Slightly poor | Slightly poor |
| 1 | Poor | Poor | Uneven | Poor | Poor |

Ranking Standards

⊚: Average score≥4.5

○: 4.5>Average score≥3.5

Δ: 3.5>Average score≥2.5

×: 2.5>Average score≥1.5

××: 1.5>Average score

TABLE 2

Assessment results

| | Spreadability | Softness | Adhesion | Mixing state | Skin configuration correcting effect (soft focus effect) |
|---|---|---|---|---|---|
| Example 1 | ⊚ | ⊚ | ⊚ | ⊚ | ⊚ |
| Example 2 | ⊚ | ⊚ | ⊚ | ⊚ | ○ |
| Example 3 | ○ | ○ | ⊚ | ⊚ | ○ |
| Example 4 | ○ | ⊚ | ○ | ⊚ | ○ |
| Example 5 | ⊚ | ⊚ | ○ | ⊚ | ○ |
| Comparative Example 1 | Δ | X | ○ | ⊚ | ⊚ |
| Comparative Example 2 | ⊚ | ○ | ⊚ | Δ | X |
| Comparative Example 3 | X | X | X | Δ | XX |
| Comparative Example 4 | Δ | Δ | Δ | Δ | Δ |
| Comparative Example 5 | ⊚ | ○ | X | ⊚ | XX |

As is apparent from Table 2, it was substantiated that compared with the powders of the comparative examples, the composite particles according to the present invention were good in usability such as spreadability (flatting property), softness (touch feel) and adhesion (adherence, evenness), were also good in the mixing state (dispersibility) of powder, and also excellent in skin configuration correcting effect (soft focus effect).

Examples 6 & 7, Comparative Examples 6 & 7

Powder Foundations

Using the composite particles obtained in some examples and the powders of some comparative examples, powder foundations were formulated in accordance with the formulas shown in Table 3.

TABLE 3

| Formulas (wt %) | Example 6 | Example 7 | Comparative Example 6 | Comparative Example 7 |
|---|---|---|---|---|
| (1) Composite particles of barium sulfate (Example 1) | 5.0 | | | |
| (2) Composite particles of sericite (Example 2) | 32.0 | 32.0 | | |
| (3) Composite particles of hydrated silicon dioxide (Example 3) | | 5.0 | | |
| (4) Composite particles of crosslinked spherical polymethyl methacrylate (Example 5) | 5.0 | 5.0 | | |
| (5) Talc treated with metallic soap | 31.0 | 31.0 | 31.0 | 31.0 |
| (6) Titanium oxide | 10.0 | 10.0 | 10.0 | 10.0 |
| (7) Red iron oxide | 0.7 | 0.7 | 0.7 | 0.7 |
| (8) Yellow iron oxide | 1.2 | 1.2 | 1.2 | 1.2 |
| (9) Black iron oxide | 0.1 | 0.1 | 0.1 | 0.1 |
| (10) Barium sulfate (Comparative Example 1) | | | 5.0 | |
| (11) Sericite treated with metallic soap (Comparative Example 2) | | | 32.0 | 32.0 |
| (12) Silicon dioxide treated with methylhydrogenpolysiloxane (Comparative Example 3) | | | | 5.0 |
| (13) Composite particles of crosslinked spherical polymethyl methacrylate according to the present invention (Comparative Example 5) | | | 5.0 | 5.0 |
| (14) Dimethylpolysiloxane (6 mm²/s (25° C.)) | 7.0 | 7.0 | 7.0 | 7.0 |
| (15) Glyceryl trioctanoate | 1.5 | 1.5 | 1.5 | 1.5 |
| (16) Dipentaerythritol fatty acid ester | 5 | 5 | 5 | 5 |
| (17) Antioxidant | q.s. | q.s. | q.s. | q.s. |
| (18) Antiseptic | q.s. | q.s. | q.s. | q.s. |
| (19) Fragrance | q.s. | q.s. | q.s. | q.s. |
| Total | 100.0 | 100.0 | 100.0 | 100.0 |

(Procedure)

The ingredients (1) to (13) were charged in a Henschel mixer, and were stirred and mixed. The ingredients (14) to (18), which had been prepared into a uniform solution on the side, were added to the resulting mixture, and stirring and mixing was continued further. To the thus-obtained mixture, the ingredient (19) was added. The resulting mixture was crushed in a hammer mill, and then compression-formed in a predetermined aluminum pan to obtain a powder foundation. With respect to the thus-obtained powder foundation, the following assessment was performed.

(Assessment)

By a panel of 50 female expert assessors, each powder foundation obtained as described above was assessed in accordance with the assessment standards shown in Table 4 for spreadability (flatting property), softness (touch feel), adhesion (adherence, evenness), naturalness of cosmetic finish (bare skin feel) and makeup retention (long-lasting property) upon application of the cosmetic sample. Based on the average scores by the 50 female expert assessors, the results were ranked in accordance with the below-described ranking standards. The results are shown in Table 5.

TABLE 4

Assessment standards

| Scores | Spreadability | Softness | Adhesion | Naturalness | Makeup retention |
|---|---|---|---|---|---|
| 5 | Good | Good | None | Natural | Good |
| 4 | Slightly good | Slightly good | Substantially none | Slightly natural | Slightly good |
| 3 | Moderate | Moderate | Moderate | Moderate | Moderate |
| 2 | Slightly poor | Slightly poor | Not satisfactory | Slightly unnatural | Slightly poor |
| 1 | Poor | Not felt | Uneven | Unnatural | Poor |

Ranking Standards
◎: Average score≥4.5
○: 4.5>Average score≥3.5
Δ: 3.5>Average score≥2.5
×: 2.5>Average score≥1.5
××: 1.5>Average score

TABLE 5

| | Example | | Comparative Example | |
|---|---|---|---|---|
| | 6 | 7 | 6 | 7 |
| Spreadability | ◎ | ○ | ○ | Δ |
| Softness | ◎ | ◎ | Δ | X |
| Adhesion | ◎ | ○ | Δ | Δ |
| Naturalness | ◎ | ◎ | ○ | Δ |
| Makeup retention | ◎ | ◎ | X | ○ |

As is apparent from Table 5, it was substantiated that compared with Comparative Examples 6 and 7, Examples 6 and 7 were good in usability, gave a natural finish, were also good in makeup retention, and therefore, were excellent powder foundations. Examples of cosmetics with composite particles of the present invention mixed therein will be described below.

Example 8

Oil-in-Water Cream

| Formula | Weight (%) |
|---|---|
| 1. Composition composed of crosslinking dimethylpolysiloxane and silicone oil (Note 1) | 10.0 |
| 2. Glyceryl trioctanoate | 5.0 |
| 3. Composite particles of Example 5 | 1.0 |
| 4. Dipropylene glycol | 7.0 |
| 5. Glycerin | 5.0 |
| 6. Methylcellulose (2% aqueous solution) (Note 2) | 7.0 |
| 7. Polyacrylamide emulsifier (Note 3) | 2.0 |
| 8. Antiseptic | q.s. |
| 9. Fragrance | q.s. |
| 10. Purified water | 63.0 |
| Total | 100.0 |

(Note 1) Composition composed of crosslinking dimethylpolysiloxane and silicone oil: "KSG-16" (product of Shin-Etsu Chemical Co., Ltd.)
(Note 2) Methylcellulose: "METOLOSE SM-4000" (product of Shin-Etsu Chemical Co., Ltd.)
(Note 3) Polyacrylamide emulsifier: "SEPPIGEL 305" (product of SEPIC Inc.)

(Procedure)
A: The ingredients 4 to 10 were mixed.
B: The ingredients 1 to 3 were mixed, and then added to A, followed by emulsification with stirring.

An oil-in-water cream obtained as described above was confirmed to be fine in texture, light in spreadability and free of tackiness or greasiness, to give a soft use feel, to have skin configuration correcting effect, to be very good in makeup retention, to remain unchanged at varied temperatures or with time, and hence, to be excellent in stability.

Example 9

Water-in-Oil Cream

| Formula | Weight (%) |
|---|---|
| 1. Dimethylpolysiloxane (6 mm$^2$/s (25° C.)) | 6.0 |
| 2. Methylphenylpolysiloxane | 4.0 |
| 3. Squalane | 5.0 |
| 4. Neopentyl glycol dioctanoate | 3.0 |
| 5. Polyether-modified silicone (Note 1) | 3.0 |
| 6. Composite particles of Example 1 | 2.0 |
| 7. Composite particles of Example 4 | 0.7 |
| 8. Glycerin | 10.0 |
| 9. Antiseptic | q.s. |
| 10. Fragrance | q.s. |
| 11. Purified water | Balance |
| Total | 100.0 |

(Note 1) Polyether-modified silicone: "KS-6012" (product of Shin-Etsu Chemical Co., Ltd.)

(Procedure)
A: The ingredients 1 to 5 were mixed, the ingredients 6 and 7 were added, and the resultant mixture was prepared into a uniform mixture.
B: The ingredients 8, 9 and 11 were mixed into a solution.
C: Under stirring, the solution of B was gradually added to the mixture of A. Subsequent to emulsification, the ingredient 10 was added to obtain a cream.

The water-in-oil cream obtained as described above was confirmed to be fine in texture, light in spreadability and free of tackiness or greasiness, to give a soft use feel, to have skin configuration correcting effect, to be very good in makeup retention, to remain unchanged at varied temperatures or with time, and hence, to be excellent in stability.

Example 10

Water-in-Oil Cream

| Formula | Weight (%) |
|---|---|
| 1. Composition composed of alkyl-modified crosslinking polyether-modified silicone and liquid paraffin (Note 1) | 6.0 |
| 2. Liquid paraffin | 13.5 |
| 3. Macadamia nut oil | 5.0 |
| 4. Alkyl/polyether-co-modified silicone (Note 2) | 0.5 |
| 5. Particles obtained by coating surfaces of silicone elastomer with polymethylsilsesquioxane (Note 3) | 3.0 |
| 6. Composite particles of Example 3 | 2.0 |
| 7. Sodium citrate | 0.2 |
| 8. Propylene glycol | 8.0 |

-continued

| Formula | Weight (%) |
| --- | --- |
| 9. Glycerin | 3.0 |
| 10. Antiseptic | q.s. |
| 11. Fragrance | q.s. |
| 12. Purified water | 58.8 |
| Total | 100.0 |

(Note 1) Composition composed of alkyl-modified crosslinking polyether-modified silicone and liquid paraffin: "KSG-310" (product of Shin-Etsu Chemical Co., Ltd.)
(Note 2) Alkyl/polyether-co-modified silicone: "KF-6038" (product of Shin-Etsu Chemical Co., Ltd.)
(Note 3) Particles obtained by coating surfaces of silicone elastomer with polymethylsilsesquioxane "KSP-100" (product of Shin-Etsu Chemical Co., Ltd.)

(Procedure)

A: The ingredients 1 to 6 were mixed.

B: The ingredients 7 to 12 were mixed into a solution, and were added to the mixture of A, followed by emulsification with stirring.

The water-in-oil cream obtained as described above was confirmed to be fine in texture, light in spreadability and free of tackiness or greasiness, to give a soft use feel, to have skin configuration correcting effect, to be very good in makeup retention, to remain unchanged at varied temperatures or with time, and hence, to be excellent in stability.

Example 11

Water-in-Oil Cream

| Formula | Weight (%) |
| --- | --- |
| 1. Decamethylcyclopentasiloxane | 16.0 |
| 2. Dimethylpolysiloxane (6 mm$^2$/s (25° C.)) | 4.0 |
| 3. Polyether-modified silicone (Note 1) | 5.0 |
| 4. POE (5) octyl dodecyl ether | 1.0 |
| 5. Polyoxyethylene sorbitan monostearate (20 E.O.) | 0.5 |
| 6. Composite particles of Example 3 | 2.0 |
| 7. Composite particles of Example 1 | 10.0 |
| 8. Liquid paraffin | 2.0 |
| 9. Macadamia nut oil | 1.0 |
| 10. *Scutellaria baicalensis* root extract (Note 2) | 1.0 |
| 11. Gentian extract (Note 3) | 0.5 |
| 12. Ethanol | 5.0 |
| 13. 1,3-Butylene glycol | 2.0 |
| 14. Antiseptic | q.s. |
| 15. Fragrance | q.s. |
| 16. Purified water | Balance |
| Total | 100.0 |

(Note 1) Polyether-modified silicone: "KF-6017" (product of Shin-Etsu Chemical Co., Ltd.)
(Note 2) *Scutellaria baicalensis* root extract; 50%, extracted with 1,3-butylene glycol-water.
(Note 3) Gentian extract; 20%, extracted with ethanol-water.

(Procedure)

A: The ingredients 6 to 9 were mixed into a uniform dispersion.

B: The ingredients 1 to 5 were mixed, and to the resultant mixture, the dispersion of A was added.

C: After the ingredients 10 to 14 and 16 were mixed, the mixture of B was added, followed by emulsification.

D: The ingredient 15 was added to the emulsion of C to obtain a cream.

The water-in-oil cream obtained as described above was fine in texture, free of tackiness, light in spreadability, gave an excellent adhesion feel and a soft use feel, had skin configuration correcting effect, and was also very good in makeup retention. It was also confirmed to remain unchanged at varied temperatures or with time, and hence, to be also excellent in stability.

Example 12

Eyeliner

| Formula | Weight (%) |
| --- | --- |
| 1. Decamethylcyclopentasiloxane | 39.0 |
| 2. Polyether-modified silicone (Note 1) | 3.0 |
| 3. Organosilicone resin (Note 2) | 15.0 |
| 4. Montmorillonite modified with dioctadecyldimethylammonium salt | 3.0 |
| 5. Black iron oxide treated with Methylhydrogenpolysiloxane | 8.0 |
| 6. Composite particles of Example 5 | 2.0 |
| 7. 1,3-Butylene glycol | 5.0 |
| 8. Sodium dehydroacetate | q.s. |
| 9. Antiseptic | q.s. |
| 10. Purified water | Balance |
| Total | 100.0 |

(Note 1) Polyether-modified silicone: "KF-6017" (product of Shin-Etsu Chemical Co., Ltd.)
(Note 2) Organosilicone resin: "KF-7312J" (product of Shin-Etsu Chemical Co., Ltd.)

(Procedure)

A: The ingredients 1 to 4 were mixed, the ingredients 5 and 6 were added, and the resulting mixture was mixed into a uniform dispersion.

B: The ingredients 7 to 10 were mixed.

C: The mixture of B was gradually added to the dispersion of A, followed by emulsification to obtain an eyeliner.

The eyeliner obtained as described above was light in spreadability, was easy to draw on, gave a sensation of coolness and cleanliness, and also gave a non-tacky use feel. In addition, it remained unchanged at varied temperatures or with time, and therefore, was very good in both usability and stability. It was, hence, confirmed to be very good in makeup retention, to say nothing of its excellence in water resistance and perspiration resistance.

Example 13

Foundation

| Formula | Weight (%) |
| --- | --- |
| 1. Decamethylcyclopentasiloxane | 45.0 |
| 2. Dimethylpolysiloxane (6 mm$^2$/s (25° C.)) | 5.0 |
| 3. Polyether-modified silicone (Note 1) | 3.5 |
| 4. Montmorillonite modified with octadecyldimethylbenzylammonium salt | 1.5 |
| 5. Composite particles of Example 1 | 14.5 |
| 6. Iron oxide treated with triethoxysilylethyl polydimethylsiloxyethyl hexyl dimethicone (Note 2) | 2.5 |
| 7. Titanium oxide treated with triethoxysilylethyl polydimethylsiloxyethyl hexyl dimethicone (Note 2) | 7.5 |
| 8. Dipropylene glycol | 5.0 |
| 9. Methyl paraoxybenzoate | 0.3 |
| 10. Fragrance | q.s. |
| 11. Purified water | Balance |
| Total | 100.0 |

(Note 1) Polyether-modified silicone: "KF-6017" (product of Shin-Etsu Chemical Co., Ltd.)
(Note 2) Triethoxysilylethyl polydimethylsiloxyethyl hexyl dimethicone: "KF-9909" (product of Shin-Etsu Chemical Co., Ltd.)

(Procedure)

A: The ingredients 1 to 4 were mixed under heat, the ingredients 5 to 7 were added, and the resultant mixture was made uniform.
B: The ingredients 8 to 9 and 11 were mixed into a solution.
C: Under stirring, the solution of B was gradually added to the mixture of A. Subsequent to cooling, the ingredient 10 was added to obtain a foundation.

The foundation obtained as described above was confirmed to be fine in texture, light in spreadability and free of tackiness or greasiness, to give a soft use feel, to have skin configuration correcting effect, to be good in makeup retention, to remain unchanged at varied temperatures or with time, and hence, to be also excellent in stability.

Example 14

Eye Shadow

| Formula | Weight (%) |
| --- | --- |
| 1. Decamethylcyclopentasiloxane | 15.0 |
| 2. Dimethylpolysiloxane (6 mm$^2$/s (25° C.)) | 10.0 |
| 3. Polyether-modified branched silicone (Note 1) | 2.0 |
| 4. PEG (10) lauryl ether | 0.5 |
| 5. Composite particles of Example 2 | 6.2 |
| 6. Composite particles of Example 1 | 4.0 |
| 7. Composite particles of Example 5 | 6.0 |
| 8. Inorganic color pigment treated with methylhydrogenpolysiloxane | q.s. |
| 9. Sodium chloride | 2.0 |
| 10. Propylene glycol | 8.0 |
| 11. Antiseptic | q.s. |
| 12. Fragrance | q.s. |
| 13. Purified water | Balance |
| Total | 100.0 |

(Note 1) Polyether-modified branched silicone: "KF-6028" (product of Shin-Etsu Chemical Co., Ltd.)

(Procedure)

A: The ingredients 1 to 4 were mixed, the ingredients 5 to 8 were added, and the resulting mixture was mixed into a uniform dispersion.
B: The ingredients 9 to 11 and 13 were mixed into a uniform solution.
C: Under stirring, the solution of B was gradually added to the dispersion of A, and the ingredient 12 was then added to obtain an eye shadow.

The eye shadow obtained as described above was light in spreadability, was free of greasiness or powdery properties, and gave a soft use feel. It was also confirmed to be good in water resistance, water repellency, perspiration resistance and makeup retention, to be resistant to makeup running, to remain unchanged at varied temperatures or with time, and hence, to be also excellent in stability.

Example 15

Lipstick

| Formula | Weight (%) |
| --- | --- |
| 1. Candelilla wax | 8.0 |
| 2. Polyethylene wax | 8.0 |
| 3. Long-chain alkyl-containing acryl silicone resin (Note 1) | 12.0 |
| 4. Methylphenylpolysiloxane (Note 2) | 3.0 |
| 5. Isotridecyl isononanoate | 20.0 |
| 6. Glyceryl isostearate | 16.0 |
| 7. Polyglyceryl triisostearate | 28.5 |
| 8. Composite particles of Example 3 | 0.8 |
| 9. Composite particles of Example 5 | 1.5 |
| 10. Organic pigment | q.s. |
| 11. Fragrance | q.s. |
| Total | 100.0 |

(Note 1) Long-chain alkyl-containing acryl silicone Resin: "KP-561P" (product of Shin-Etsu Chemical Co., Ltd.)
(Note 2) Methylphenylpolysiloxane: "KF-54" (product of Shin-Etsu Chemical Co., Ltd.)

(Procedure)

A: The ingredients 1 to 6 and a portion of the ingredient 7 were mixed under heat into a solution.
B: The ingredients 8 to 10 and the rest of the ingredient 7 were mixed into a uniform mixture, the mixture was added to the solution of A, and the resulting mixture was formed into a homogeneous mixture.
C: The ingredient 12 was added to the homogeneous mixture of B to obtain a lipstick.

The lipstick obtained as described above was light in spreadability, was free of greasiness or powdery properties, and gave a soft use feel. In addition, it was good in water resistance and water repellency and was good in makeup retention, and was also excellent in stability.

Example 16

Eyeliner

| Formula | Weight (%) |
| --- | --- |
| 1. Decamethylcyclopentasiloxane | 6.0 |
| 2. Dimethylpolysiloxane (6 mm$^2$/s (25° C.)) | 5.0 |
| 3. Jojoba oil | 2.0 |
| 4. Polyether-modified silicone (Note 1) | 1.0 |
| 5. Alkyl/polyether-co-modified silicone (Note 2) | 1.0 |
| 6. Acryl silicone resin (Note 3) | 15.0 |
| 7. Composite particles of Example 2 | 2.0 |
| 8. Black iron oxide treated with Methylhydrogenpolysiloxane | 18.0 |
| 9. Ethanol | 5.0 |
| 10. Antiseptic | q.s. |
| 11. Purified water | Balance |
| Total | 100.0 |

(Note 1) Polyether-modified silicone: "KF-6017" (product of Shin-Etsu Chemical Co., Ltd.)
(Note 2) Alkyl/polyether-co-modified silicone: "KF-6038" (product of Shin-Etsu Chemical Co., Ltd.)
(Note 3) Acryl silicone resin: "KP-545" (product of Shin-Etsu Chemical Co., Ltd.)

(Procedure)

A: The ingredients 1 to 6 were stirred and mixed, and to the resultant mixture, the ingredients 7 and 8 were added, followed by preparation into a uniform dispersion.
B: The ingredients 9 to 11 were mixed into a solution.
C: Under stirring, the solution of B was gradually added to the dispersion of A, followed by emulsification to obtain an eyeliner.

The eyeliner obtained as described above was light in spreadability, was free of greasiness or powdery properties, gave a soft use feel, was good in water resistance, water repellency and perspiration resistance, and was resistance to makeup running. It was also confirmed to remain unchanged at varied temperatures or with time and hence, to be excellent in stability.

Example 17

Emulsified Liquid Foundation

| Formula | Weight (%) |
| --- | --- |
| 1. Dimethylpolysiloxane (6 mm²/s (25° C.)) | 4.5 |
| 2. Decamethylcyclopentasiloxane | 15.0 |
| 3. Squalane | 4.0 |
| 4. Neopentyl glycol dioctanoate | 3.0 |
| 5. Diglyceryl myristate isostearate | 2.0 |
| 6. α-Monoisostearyl glyceryl ether | 1.0 |
| 7. Polyether-modified silicone (Note 1) | 1.0 |
| 8. Alkyl/polyether-co-modified silicone (Note 2) | 0.5 |
| 9. Aluminum distearate salt | 0.2 |
| 10. Composite particles of Example 2 | 2.0 |
| 11. Composite particles of Example 1 | 5.0 |
| 12. Iron oxide pigment treated with methylhydrogenpolysiloxane | q.s. |
| 13. Glycerin | 3.0 |
| 14. Antiseptic | q.s. |
| 15. Fragrance | q.s. |
| 16. Purified water | Balance |
| Total | 100.0 |

(Note 1) Polyether-modified silicone: "KF-6017" (product of Shin-Etsu Chemical Co., Ltd.)
(Note 2) Alkyl/polyether-co-modified silicone: "KF-6038" (product of Shin-Etsu Chemical Co., Ltd.)

(Procedure)
A: The ingredients 1 to 9 were mixed under heat, and the ingredients 10 to 12 were added, followed by preparation into a uniform mixture.
B: The ingredients 13 to 14 and 16 were heated into a solution.
C: Under stirring, the solution of B was gradually added to the mixture of A, followed by emulsification. The resultant mixture was cooled, and the ingredient 15 was added to obtain an emulsified liquid foundation.

The emulsified liquid foundation obtained as described above was confirmed to be low in viscosity, fine in texture, is light in spreadability and free of tackiness or greasiness, to give a soft use feel, to have skin configuration correcting effect, to be good in makeup retention, to remain unchanged at varied temperatures or with time, and hence, to be also excellent in stability.

Example 18

Liquid Foundation

| Formula | Weight (%) |
| --- | --- |
| 1. Decamethylcyclopentasiloxane | 16.0 |
| 2. Dimethylpolysiloxane (6 mm²/s (25° C.)) | 8.0 |
| 3. Octyl paramethoxycinnamate | 3.0 |
| 4. 12-Hydroxystearic acid | 1.0 |
| 5. Fluorine-modified silicone (Note 1) | 15.0 |
| 6. Alkyl fluoride/polyether-co-modified Silicone (Note 2) | 5.0 |
| 7. Spherical polymethylsilsesquioxane powder (Note 3) | 1.0 |
| 8. Composite particles of Example 5 | 4.0 |
| 9. Composite particles of Example 1 | 2.0 |
| 10. Iron oxide pigment treated with methylhydrogenpolysiloxane | q.s. |
| 11. Ethanol | 15.0 |
| 12. Glycerin | 3.0 |
| 13. Magnesium sulfate | 1.0 |
| 14. Antiseptic | q.s. |
| 15. Fragrance | q.s. |
| 16. Purified water | Balance |
| Total | 100.0 |

(Note 1) Fluorine-modified silicone: "FL-50" (product of Shin-Etsu Chemical Co., Ltd.)
(Note 2) Alkyl fluoride-polyether-co-modified silicone: "FPD-4694" (product of Shin-Etsu Chemical Co., Ltd.)
(Note 3) Spherical polymethylsilsesquioxane powder: "KMP-590" (product of Shin-Etsu Chemical Co., Ltd.)

(Procedure)
A: The ingredients 7 to 10 were mixed into a uniform mixture.
B: The ingredients 1 to 6 were heated to 70° C., at which they were mixed. To the resulting mixture, the mixture of A was added, followed by mixing into a dispersion.
C: The ingredients 11 to 14 and 16 were heated to 40° C., and were then gradually added to the dispersion of B. The resulting mixture was emulsified. The emulsion was cooled, and the ingredient 15 was added to obtain a liquid foundation.

The liquid foundation obtained as described above was confirmed to be free of tackiness and light in spreadability, to give a soft use feel, to have skin configuration correcting effect, to remain unchanged at varied temperatures or with time, and hence, to be very good in stability.

Example 19

Eyeliner

| Formula | Weight (%) |
| --- | --- |
| 1. Decamethylcyclopentasiloxane | 22.0 |
| 2. Dimethylpolysiloxane (6 mm²/s (25° C.)) | 5.0 |
| 3. Black iron oxide treated with methylhydrogenpolysiloxane | 20.0 |
| 4. Composite particles of Example 4 | 1.0 |
| 5. Organosilicone resin (Note 1) | 10.0 |
| 6. Vitamin E acetate | 0.2 |
| 7. Jojoba oil | 2.0 |
| 8. Bentonite | 3.0 |
| 9. Polyether-modified silicone (Note 2) | 2.0 |
| 10. Ethanol | 3.0 |
| 11. 1,3-butylene glycol | 5.0 |
| 12. Antiseptic | q.s. |
| 13. Purified water | Balance |
| Total | 100.0 |

(Note 1) Organosilicone resin: "KF-7312J" (product of Shin-Etsu Chemical Co., Ltd.)
(Note 2) Polyether-modified silicone: "KF-6017" (product of Shin-Etsu Chemical Co., Ltd.)

(Procedure)
A: The ingredients 1 to 2 and 5 to 9 were mixed, the ingredients 3 and 4 were added, and the resulting mixture was mixed into a uniform dispersion.
B: The ingredients 10 to 13 were mixed.
C: The mixture of B was gradually added to the dispersion of A, followed by emulsification to obtain an eyeliner.

The eyeliner obtained as described above was confirmed to be light in spreadability and easy to draw on, to give a sensation of coolness and cleanliness and also a non-tacky and soft use feel, to remain unchanged at varied temperatures or with time, and to be excellent in both water resistance and perspiration resistance and therefore, very good in makeup retention.

Example 20

Foundation

| Formula | Weight (%) |
| --- | --- |
| 1. Decamethylcyclopentasiloxane | 27.0 |
| 2. Methylphenylpolysiloxane | 3.0 |
| 3. Glyceryl trioctanoate | 10.0 |
| 4. Polyether-modified silicone (Note 1) | 4.0 |
| 5. Polyglyceryl monoisostearate | 3.0 |
| 6. Composite particles of Example 1 | 8.0 |
| 7. Composite particles of Example 2 | 4.0 |
| 8. Composite particles of Example 5 | 3.0 |
| 9. Titanium oxide treated with aluminum stearate | 6.0 |
| 10. Iron oxide pigment treated with methylhydrogenpolysiloxane | q.s. |
| 11. 1,3-Butylene glycol | 7.0 |
| 12. Sodium chloride | 0.5 |
| 13. Antiseptic | q.s. |
| 14. Fragrance | q.s. |
| 15. Purified water | Balance |
| Total | 100.0 |

(Note 1) Polyether-modified silicone: "KF-6017" (product of Shin-Etsu Chemical Co., Ltd.)

(Procedure)
A: The ingredients 1 to 5 were mixed into a solution, in which the ingredients 6 to 10 were evenly dispersed.
B: After the ingredients 11 to 13 and 15 were mixed, the mixture was added to the dispersion of A, followed by emulsification.
C: The ingredient 14 was added to the emulsion of B to obtain a foundation.

The foundation obtained as described above was found to be free of tackiness and light in spreadability, to give an excellent adhesion feel and a soft use feel, to have skin configuration correcting effect, to be very good in makeup retention, to remain unchanged at varied temperatures or with time, and hence, to be also very good in stability.

Example 21

Brushing Aid (Spray)

| Formula | Weight (%) |
| --- | --- |
| 1. Isopropyl myristate | 1.0 |
| 2. Stearyltrimethylammonium chloride | 0.05 |
| 3. Composite particles of Example 5 | 3.0 |
| 4. Ethanol | 25.0 |
| 5. Fragrance | q.s. |
| 6. Propellant | Balance |
| Total | 100.0 |

(Procedure)
A: The ingredients 1 to 5 were mixed.
B: After the mixture of A was filled in an aerosol can, the ingredient 6 was filled to obtain a brushing aid.

The brushing aid (spray) obtained as described above was confirmed to give a very smooth use feel, to be excellent in long-lasting property, to be superb in powder dispersibility upon use, to provide good comb-through and glow, and therefore, to be very good.

Example 22

Hair Rinse

| Formula | Weight (%) |
| --- | --- |
| 1. Ethylene glycol distearate | 3.0 |
| 2. Cetanol | 2.0 |
| 3. Propylene glycol monostearate | 3.0 |
| 4. Dimethylpolysiloxane (100 mm$^2$/s (25° C.)) | 3.0 |
| 5. Glyceryl monostearate | 4.0 |
| 6. Polyoxyethylene (3) stearate | 4.0 |
| 7. Acetyltrimethylammonium chloride | 5.0 |
| 8. Polyoxyethylene (20) cetyl ether | 2.0 |
| 9. Composite particles of Example 5 | 2.0 |
| 10. 1,3-Butylene glycol | 5.0 |
| 11. Antiseptic | q.s. |
| 12. Fragrance | q.s. |
| 13. Purified water | Balance |
| Total | 100.0 |

(Procedure)
A: The ingredients 1 to 9 were stirred and mixed.
B: The ingredients 10 to 11 and 13 were mixed under heat.
C: The mixture of B was added to the mixture of A. Subsequent to mixing, the mixture was cooled, and the ingredient 12 was then added to obtain a hair rinse.

The hair rinse obtained as described above was confirmed to be free of greasiness or heaviness upon use, to give excellent glow to hair, to impart freely flowing, smoothness and body to hair, to provide good comb-through, and to be good in both usability and long-lasting property.

Example 23

Conditioning Shampoo

| Formula | Weight (%) |
| --- | --- |
| 1. Lauric acid amide propyldimethyl betaine aminoacetate (30%) | 15.0 |
| 2. Sodium polyoxyethylene (3) lauryl ether Sulfate (27%) | 4.0 |
| 3. Polyoxyethylene (150) distearate | 0.5 |
| 4. Cationized cellulose (4%) | 0.5 |
| 5. Glycerin | 3.0 |
| 6. Dimethylpolysiloxane (100 × 10$^6$ mm$^2$/s (25° C.)) | 1.0 |
| 7. Dimethylpolysiloxane (100 mm$^2$/s (25° C.)) | 3.0 |
| 8. Composite particles of Example 5 | 2.0 |
| 9. Antiseptic | q.s. |
| 10. Fragrance | q.s. |
| 11. Purified water | Balance |
| Total | 100.0 |

(Procedure)
A: The ingredients 1 to 5, 9 and 11 were mixed under heat.
B: The ingredients 6 to 8 were mixed into a dispersion.
C: After B was added to A, followed by mixing, the resulting mixture was cooled, and the ingredient 10 was then added to obtain a conditioning shampoo.

The conditioning shampoo obtained as described above was confirmed to be free of greasiness or heaviness upon use, to give excellent glow to hair, to impart freely flowing, smoothness and body to hair, to provide good comb-through, and to be good in both usability and long-lasting property.

Example 24

Hair Conditioner

| Formula | Weight (%) |
|---|---|
| 1. Ethylene glycol distearate | 1.0 |
| 2. Liquid paraffin | 10.0 |
| 3. Squalane | 5.0 |
| 4. Stearyl alcohol | 1.5 |
| 5. Dimethylpolysiloxane (10 mm$^2$/s (25° C.)) | 3.0 |
| 6. Stearic acid | 6.0 |
| 7. Polyoxyethylene (3) stearyl alcohol | 4.5 |
| 8. Polyoxyethylene (150) cetyl ether | 2.0 |
| 9. Composite particles of Example 5 | 1.5 |
| 10. 1,3-Butylene glycol | 6.0 |
| 11. Antiseptic | q.s. |
| 12. Fragrance | q.s. |
| 13. Purified water | Balance |
| Total | 100.0 |

(Procedure)
A: The ingredients 1 to 9 were mixed under heat.
B: The ingredients 10 to 11 and 13 were mixed into a dispersion.
C: After B was added to A, followed by mixing, the resulting mixture was cooled, and the ingredient 12 was then added to obtain a hair conditioner.

The hair conditioner obtained as described above was confirmed to be free of greasiness or heaviness upon use, to give excellent glow to hair, to impart freely flowing, smoothness and body to hair, to provide good comb-through, and to be good in both usability and long-lasting property.

Example 25

Water-in-Oil Antiperspirant

| Formula | Weight (%) |
|---|---|
| 1. Composition composed of crosslinking polyether-modified silicone and silicone oil (Note 1) | 7.0 |
| 2. Decamethylcyclopentasiloxane | 10.0 |
| 3. Glyceryl trioctanoate | 7.0 |
| 4. Dipropylene glycol | 5.0 |
| 5. Sodium citrate | 0.2 |
| 6. Aluminum zirconium tetrachlorohydrate | 18.0 |
| 7. Composite particles of Example 4 | 5.0 |
| 8. Particles obtained by coating surfaces of silicone elastomer particles with polymethylsilsesquioxane (Note 2) | 2.0 |
| 9. Fragrance | q.s. |
| 10. Purified water | 45.8 |
| Total | 100.0 |

(Note 1) Composition composed of crosslinking polyether-modified silicone and silicone oil: "KSG-210" (product of Shin-Etsu Chemical Co., Ltd.)
(Note 2) Particles obtained by coating surfaces of silicone elastomer particles with polymethylsilsesquioxane: "KSP-300" (product of Shin-Etsu Chemical Co., Ltd.)

(Procedure)
A: The ingredients 1 to 3 were mixed.
B: The ingredients 4 to 10 were mixed.
C: The mixture of B was added to the mixture of A, followed by emulsification.

The water-in-oil antiperspirant obtained as described above was light in spreadability and free of tackiness or greasiness, to remain unchanged with temperature or time, and hence, to be very good in both usability and stability.

Example 26

Roll-on Antiperspirant

| Formula | Weight (%) |
|---|---|
| 1. Composition composed of crosslinking polyether-modified silicone and silicone oil (Note 1) | 20.0 |
| 2. Dimethylpolysiloxane (6 mm$^2$/s (25° C.)) | 10.0 |
| 3. Composition composed of crosslinking Dimethylpolysiloxane and silicone oil (Note 2) | 15.0 |
| 4. Decamethylcyclopentasiloxane | 30.0 |
| 5. Aluminum zirconium tetrachlorohydrate | 20.0 |
| 6. Composite particles of Example 5 | 5.0 |
| 7. Fragrance | q.s. |
| Total | 100.0 |

(Note 1) Composition composed of crosslinking polyether-modified silicone and silicone oil: "KSG-210" (product of Shin-Etsu Chemical Co., Ltd.)
(Note 2) Composition composed of crosslinking Dimethylpolysiloxane and silicone oil: "KSG-15" (product of Shin-Etsu Chemical Co., Ltd.)

(Procedure)
A: The ingredients 1 to 4 were mixed.
B: The ingredients 5 to 7 were added to A, and the resulting mixture was stirred into a homogeneous dispersion.

The roll-on antiperspirant obtained as described above was light in spreadability and free of tackiness or greasiness, to remain unchanged with temperature or time, and hence, to be very good in both usability and stability.

Example 27

Sunscreen Lotion

| Formula | Weight (%) |
|---|---|
| 1. Decamethylcyclopentasiloxane | 20.0 |
| 2. Methylphenylpolysiloxane | 3.0 |
| 3. Sorbitan monoisostearate | 1.0 |
| 4. Polyether-modified silicone (Note 1) | 0.5 |
| 5. Trimethylsiloxysilicic acid (Note 2) | 1.0 |
| 6. Octyl paramethoxycinnamate | 4.0 |
| 7. Composite particles of Example 1 | 2.0 |
| 8. Fine particulate titanium oxide treated with aluminum stearate | 6.0 |
| 9. Sorbitol | 2.0 |
| 10. Sodium chloride | 2.0 |
| 11. Antiseptic | q.s. |
| 12. Fragrance | q.s. |
| 13. Purified water | Balance |
| Total | 100.0 |

(Note 1) Polyether-modified silicone: "KF-6015" (product of Shin-Etsu Chemical Co., Ltd.)
(Note 2) Trimethylsiloxysilicic acid: "X-21-5250" (product of Shin-Etsu Chemical Co., Ltd.)

(Procedure)
A: The ingredients 1 to 6 were mixed under heat, the ingredients 7 and 8 were evenly dispersed.
B: The ingredients 9 to 11 and 13 were mixed under heat.
C: Under stirring, B was gradually added to A, followed by emulsification. Subsequent to cooling, the ingredient 12 was added to obtain a sunscreen lotion.

The sunscreen lotion obtained as described above was fine in texture, light in spreadability and free of tackiness, to give a soft use feel, and also to have skin configuration correcting effect. In addition, it was confirmed to be good in makeup retention and to retain UV protection effect, to remain unchanged at varied temperatures or with time, and hence, to be also very good in stability.

Example 28

Sunscreen Cream

| Formula | Weight (%) |
|---|---|
| 1. Decamethylcyclopentasiloxane | 17.5 |
| 2. Acrylsilicone resin (Note 1) | 12.0 |
| 3. Glyceryl trioctanoate | 5.0 |
| 4. Octyl paramethoxycinnamate | 6.0 |
| 5. Composition composed of crosslinking polyether-modified silicone and silicone oil (Note 2) | 5.0 |
| 6. Alkyl-silicone/polyether-co-modified silicone (Note 3) | 2.5 |
| 7. Composite particles of Example 5 | 2.0 |
| 8. Fine particulate titanium oxide treated with aluminum stearate | 15.0 |
| 9. Sodium chloride | 0.5 |
| 10. 1,3-Butylene glycol | 2.0 |
| 11. Antiseptic | q.s. |
| 12. Fragrance | q.s. |
| 13. Purified water | Balance |
| Total | 100.0 |

(Note 1) Acryl silicone resin: "KP-545" (product of Shin-Etsu Chemical Co., Ltd.)
(Note 2) Composition composed of crosslinking polyether-modified silicone and silicone oil: "KSG-210" (product of Shin-Etsu Chemical Co., Ltd.)
(Note 3) Alkyl/polyether-co-modified silicone: "KF-6038" (product of Shin-Etsu Chemical Co., Ltd.)

(Procedure)

A: The ingredient 2 was added to a portion of the ingredient 1, and the resulting mixture was made uniform. The ingredient 8 was added, followed by dispersion in a bead mill.

B: The rest of the ingredient 1 and the ingredients 3 to 7 were combined into a uniform mixture.

C: The ingredients 9 to 11 and 13 were mixed into a solution.

D: C was added to B, and the resulting mixture was emulsified. In the emulsion, the dispersion of A was dispersed. The ingredient 12 was further added to obtain a sunscreen cream.

The sunscreen cream obtained as described above was free of tackiness and light in spreadability, to give an excellent adhesion feel and a soft use feel, to have skin configuration correcting effect, and to be very good in makeup retention. It was also confirmed to remain very stable at varied temperatures or with time.

Example 29

Nail Enamel

| Formula | Weight (%) |
|---|---|
| 1. Acrylsilicone resin (Note 1) | 44.5 |
| 2. Methyltrimethicone (Note 2) | 5.0 |
| 3. Nitrocellulose | 3.0 |
| 4. Camphor | 0.5 |
| 5. Acetyltributyl citrate | 1.0 |
| 6. Dimethyldistearylammonium hectorite | 0.5 |
| 7. Butyl acetate | 30.0 |

-continued

| Formula | Weight (%) |
|---|---|
| 8. Ethyl acetate | 10.0 |
| 9. Isopropyl alcohol | 5.0 |
| 10. Composite particles of Example 3 | 0.5 |
| Total | 100.0 |

(Note 1) Acryl silicone resin: "KP-549" (product of Shin-Etsu Chemical Co., Ltd.)
(Note 2) Methyltrimethicone: "TMF-1.5" (product of Shin-Etsu Chemical Co., Ltd.)

(Procedure)

A: The ingredients 7 to 9 were mixed. To the resulting mixture, the ingredients 4 to 6 were added, followed by stirring into a uniform mixture.

B: The ingredients 1 to 3 were added to A, followed by mixing.

C: The ingredient 10 was added to B to obtain a nail enamel.

The nail enamel obtained as described above was confirmed to be light in spreadability, to impart visual smoothness, to have water resistance, oil resistance and good long-lasting property, to give no pressure feel to nails, to cause no yellowing of nails, to develop no changes in cosmetic films with temperature or time, and hence, to be also very good in stability.

The invention claimed is:

1. Composite particles comprising:
100 parts by weight of core particles selected from the group consisting of inorganic particles; inorganic pigments; particles of a polyamide, polyacrylic acid-acrylic acid ester, polyester, polyethylene, polypropylene, polystyrene, styrene-acrylic acid copolymer, divinylbenzene-styrene copolymer, polyurethane, vinyl resin, urea resin, melamine resin, benzoguanamine, polymethylbenzoguanamine, tetrafluoroethylene, polymethyl methacrylate, cellulose, silk, nylon, phenol resin, epoxy resin, and polycarbonate; organic pigments; and composite particles obtained by coating the surfaces of inorganic particles with organic particles, said core particles having an average particle size of 1 to 30 μm, and
0.5 to 70 part by weight of silicone elastomer particles adhered to the surfaces of the core particles, said silicone elastomer particles having a particle size of 50 to 800 nm,
wherein the silicone elastomer particles are adhered to the surfaces of the core particles by a silicone resin binder,
the silicone elastomer is a rubber elastomer having linear organosiloxane blocks represented by the following formula (1):

$$—(R^1{}_2SiO_{2/2})_n— \quad (1)$$

in which $R^1$ is a substituted or unsubstituted monovalent hydrocarbon group having from 1 to 30 carbon atoms, and n is a positive number of from 5 to 5,000, and
the silicone resin binder is a polymer formed of one or more of structural units selected from $[R^5SiO_{3/2}]$, $[R^5{}_2SiO_{2/2}]$, $[R^5{}_3SiO_{1/2}]$ and $[SiO_{4/2}]$ and including at least $[R^5SiO_{3/2}]$ or $[SiO_{4/2}]$: in which $R^5$ is independently a monovalent organic group having from 1 to 20 carbon atoms.

2. The composite particles according to claim 1, which is obtained by adding an acidic substance or alkaline substance and a compound selected from alkoxysilanes and silanol-containing silanes and partial condensation products thereof to a mixed aqueous dispersion having the core particles and a silicone elastomer particles dispersed therein and subjecting the compound to a hydrolytic condensation reaction, thereby causing the silicone elastomer to adhere to the surfaces of the core particles.

3. The composite particles according to claim 2, wherein the mixed aqueous dispersion further comprises a surfactant.

4. A method for preparing composite particles comprising:
100 parts by weight of core particles selected from the group consisting of inorganic particles; inorganic pigments; particles of a polyamide, polyacrylic acid-acrylic acid ester, polyester, polyethylene, polypropylene, polystyrene, styrene-acrylic acid copolymer, divinylbenzene-styrene copolymer, polyurethane, vinyl resin, urea resin, melamine resin, benzoguanamine, polymethylbenzoguanamine, tetrafluoroethylene, polymethyl methacrylate, cellulose, silk, nylon, phenol resin, epoxy resin, and polycarbonate; organic pigments; and composite particles obtained by coating the surfaces of inorganic particles with organic particles, said core particles having an average particle size of 1 to 30 μm, and
0.5 to 70 part by weight of silicone elastomer particles adhered to the surfaces of the core particles, said silicone elastomer particles having a particle size of 50 to 800 nm,
wherein the silicone elastomer particles are adhered to the surfaces of the core particles by a silicone resin binder,
the silicone elastomer is a rubber elastomer having linear organosiloxane blocks represented by the following formula (1):

$$-(R^1{}_2SiO_{2/2})_n- \quad (1)$$

in which $R^1$ is a substituted or unsubstituted monovalent hydrocarbon group having from 1 to 30 carbon atoms, and n is a positive number of from 5 to 5,000, and
the silicone resin binder is a polymer formed of one or more of structural units selected from $[R^5SiO_{3/2}]$, $[R^5{}_2SiO_{2/2}]$, $[R^5{}_3SiO_{1/2}]$ and $[SiO_{4/2}]$ and including at least $[R^5SiO_{3/2}]$ or $[SiO_{4/2}]$: in which $R^5$ is independently a monovalent organic group having from 1 to 20 carbon atoms;
the method comprising the steps of:
adding an acidic substance or alkaline substance and a compound selected from alkoxysilanes and silanol-containing silanes and partial condensation products thereof to a mixed aqueous dispersion having the core particles and silicone elastomer particles dispersed therein; and subjecting the compound to a hydrolytic condensation reaction.

5. The method according to claim 4, wherein the mixed aqueous dispersion further comprises a surfactant.

6. A cosmetic composition comprising the composite particles according to claim 1.

7. A cosmetic composition comprising the composite particles according to claim 4.

8. A cosmetic composition comprising the composite particles according to claim 5.

9. The composite particles according to claim 1, wherein an amount of the silicone resin binder is 10 parts by weight or more.

10. The composite particles according to claim 1, wherein an amount of the silicone resin binder is 30 parts by weight or more.

11. The method according to claim 4, wherein an amount of the silicone resin binder is 10 parts by weight or more.

12. The method according to claim 4, wherein an amount of the silicone resin binder is 30 parts by weight or more.

13. The composite particles according to claim 1, wherein hardness of the silicone elastomer is 10 or higher as measured by a type E durometer as specified in JIS K 6253 to 90 or lower as measured by a type A durometer.

14. The composite particles according to claim 1, wherein the silicone resin is polymer formed of one or more of structural units selected from $[R^5SiO_{3/2}]$, $[R^5{}_2SiO_{2/2}]$ and $[R^5{}_3SiO_{1/2}]$, and including at least $[R^5SiO_{3/2}]$.

15. The method according to claim 4, wherein hardness of the silicone elastomer is 10 or higher as measured by a type E durometer as specified in JIS K 6253 to 90 or lower as measured by a type A durometer.

16. The method according to claim 4, wherein the silicone resin binder is a polymer formed of one or more of structural units selected from $[R^5SiO_{3/2}]$, $[R^5{}_2SiO_{2/2}]$ and $[R^5{}_3SiO_{1/2}]$, and including at least $[R^5SiO_{3/2}]$.

* * * * *